(12) United States Patent
Flom et al.

(10) Patent No.: US 10,123,794 B2
(45) Date of Patent: Nov. 13, 2018

(54) METHOD AND APPARATUS FOR PASSING SUTURE THROUGH TISSUE

(75) Inventors: James Flom, San Carlos, CA (US); Roger Pisarnwongs, Valencia, CA (US); Thomas Weisel, Ventura, CA (US); Chris Pamichev, Cupertino, CA (US)

(73) Assignee: Pivot Medical, Inc., Sunnyvale, CA (US)

(*) Notice: Subject to any disclaimer, the term of this patent is extended or adjusted under 35 U.S.C. 154(b) by 717 days.

(21) Appl. No.: 13/230,652

(22) Filed: Sep. 12, 2011

(65) Prior Publication Data

US 2012/0123448 A1    May 17, 2012

Related U.S. Application Data

(60) Provisional application No. 61/384,423, filed on Sep. 20, 2010, provisional application No. 61/473,219, (Continued)

(51) Int. Cl.
*A61B 17/04* (2006.01)
*A61B 17/06* (2006.01)
(Continued)

(52) U.S. Cl.
CPC ...... *A61B 17/0483* (2013.01); *A61B 17/0469* (2013.01); *A61B 17/0485* (2013.01); (Continued)

(58) Field of Classification Search
CPC ............ A61B 17/0485; A61B 17/0483; A61B 17/0469
(Continued)

(56) References Cited

U.S. PATENT DOCUMENTS 292,195 A    1/1884 Austin et al.
1,545,682 A    7/1925 Nelson
(Continued)

FOREIGN PATENT DOCUMENTS

DE    25 32 242    2/1977
EP    0769272    4/1997
(Continued)

OTHER PUBLICATIONS

Acufex Microsurgical Product Catalog, 1995.
(Continued)

*Primary Examiner* — Thomas McEvoy
(74) *Attorney, Agent, or Firm* — Pandiscio & Pandiscio

(57) ABSTRACT

A suture passer comprising:
a hollow tube, the hollow tube comprising a distal end, a proximal end, a lumen extending from the distal end to the proximal end, and a window formed in the sidewall of the hollow tube, the window communicating with the lumen; and
a clamping rod slidably received in the lumen of the hollow tube, the clamping rod comprising a distal end and a proximal end, the distal end being bifurcated into a first arm and a second arm, one of the first and second arms extending distally of the other of the first and second arms and including a clamping surface, and at least one of the first and second arms being outwardly biased such that when the clamping rod is moved distally so that the distal end of the at least one outwardly biased arm is adjacent to the window, the distal end of the at least one outwardly biased arm extends outwardly through the window.

44 Claims, 65 Drawing Sheets

Related U.S. Application Data filed on Apr. 8, 2011, provisional application No. 61/495,441, filed on Jun. 10, 2011, provisional application No. 61/381,787, filed on Sep. 10, 2010.

(51) Int. Cl.
   *A61B 17/00* (2006.01)
   *A61B 17/30* (2006.01)

(52) U.S. Cl.
   CPC .............. *A61B 17/06109* (2013.01); *A61B 2017/00862* (2013.01); *A61B 2017/00867* (2013.01); *A61B 2017/061* (2013.01); *A61B 2017/06009* (2013.01); *A61B 2017/06042* (2013.01); *A61B 2017/306* (2013.01)

(58) Field of Classification Search
   USPC .................................. 606/144, 148, 201–211
   See application file for complete search history.

(56) References Cited

U.S. PATENT DOCUMENTS

| | | |
|---|---|---|
| 1,583,271 A | 5/1926 | Biro |
| 2,363,334 A | 11/1944 | Jones |
| 2,496,111 A | 1/1950 | Turkel |
| 2,738,790 A | 3/1956 | Todt, Sr. et al. |
| 2,959,172 A | 11/1960 | Held |
| 3,630,192 A | 12/1971 | Jamshidi |
| 3,877,434 A | 4/1975 | Ferguson et al. |
| 3,929,123 A | 12/1975 | Jamshidi |
| 4,174,715 A | 11/1979 | Hasson |
| 4,372,302 A | 2/1983 | Akerlund |
| 4,427,014 A | 1/1984 | Bel et al. |
| 4,602,635 A | 7/1986 | Mulhollan et al. |
| 4,641,652 A | 2/1987 | Hutterer et al. |
| 4,712,545 A | 12/1987 | Honkanen |
| 4,779,616 A | 10/1988 | Johnson |
| 4,781,190 A | 11/1988 | Lee |
| 4,784,139 A | 11/1988 | Demos |
| 4,923,461 A | 5/1990 | Caspari et al. |
| 4,957,498 A | 9/1990 | Caspari et al. |
| 4,976,269 A | 12/1990 | Mehl |
| 4,986,279 A | 1/1991 | O'Neill |
| 5,015,250 A | 5/1991 | Foster |
| 5,036,860 A | 8/1991 | Leigh et al. |
| 5,059,201 A | 10/1991 | Asnis |
| 5,090,419 A | 2/1992 | Palestrant |
| 5,149,329 A | 9/1992 | Richardson |
| 5,176,700 A | 1/1993 | Brown et al. |
| 5,181,919 A | 1/1993 | Bergman et al. |
| 5,201,741 A | 4/1993 | Dulebohn |
| 5,222,508 A | 6/1993 | Contarini |
| 5,222,977 A | 6/1993 | Esser |
| 5,250,054 A | 10/1993 | Li |
| 5,250,055 A | 10/1993 | Moore et al. |
| 5,281,237 A | 1/1994 | Gimpelson |
| 5,304,203 A | 4/1994 | El-Mallawany et al. |
| 5,312,422 A | 5/1994 | Trott |
| 5,364,410 A | 11/1994 | Failla et al. |
| 5,376,096 A | 12/1994 | Foster |
| 5,387,227 A | 2/1995 | Grice |
| 5,405,354 A | 4/1995 | Sarrett |
| 5,411,519 A | 5/1995 | Tovey et al. |
| 5,437,681 A | 8/1995 | Meade et al. |
| 5,439,467 A | 8/1995 | Benderev et al. |
| 5,447,512 A | 9/1995 | Wilson et al. |
| 5,499,991 A | 3/1996 | Garman et al. |
| 5,514,148 A | 5/1996 | Smith, III |
| 5,520,703 A | 5/1996 | Essig et al. |
| 5,522,830 A | 6/1996 | Aranyi |
| 5,569,269 A | 10/1996 | Hart et al. |
| 5,571,119 A | 11/1996 | Atala |
| 5,573,542 A | 11/1996 | Stevens |
| 5,618,290 A | 4/1997 | Toy et al. |
| 5,626,597 A | 5/1997 | Urban et al. |
| 5,628,757 A | 5/1997 | Hasson |
| 5,643,292 A | 7/1997 | Hart |
| 5,649,939 A | 7/1997 | Reddick |
| 5,653,716 A | 8/1997 | Malo et al. |
| 5,658,299 A | 8/1997 | Hart |
| 5,716,367 A | 2/1998 | Koike et al. |
| 5,722,981 A | 3/1998 | Stevens |
| 5,741,278 A | 4/1998 | Stevens |
| 5,746,759 A | 5/1998 | Meade et al. |
| 5,772,672 A | 6/1998 | Toy et al. |
| 5,797,928 A | 8/1998 | Kogasaka |
| 5,810,865 A | 9/1998 | Koscher et al. |
| 5,817,111 A | 10/1998 | Riza |
| 5,827,299 A | 10/1998 | Thomason et al. |
| 5,830,220 A | 11/1998 | Wan et al. |
| 5,893,873 A | 4/1999 | Rader et al. |
| 5,899,911 A | 5/1999 | Carter |
| 5,904,692 A | 5/1999 | Steckel et al. |
| 5,910,148 A | 6/1999 | Reimels et al. |
| 5,919,202 A | 7/1999 | Yoon |
| 5,922,001 A | 7/1999 | Yoon |
| 5,922,002 A | 7/1999 | Yoon |
| 5,928,255 A | 7/1999 | Meade et al. |
| 5,951,575 A | 9/1999 | Bolduc et al. |
| 5,954,734 A | 9/1999 | Thomason et al. |
| 5,976,161 A | 11/1999 | Kirsch et al. |
| 5,984,932 A | 11/1999 | Yoon |
| 5,984,938 A | 11/1999 | Yoon |
| 5,984,939 A | 11/1999 | Yeon |
| 5,993,466 A | 11/1999 | Yoon |
| 6,022,360 A | 2/2000 | Reimels et al. |
| 6,074,403 A | 6/2000 | Nord |
| 6,080,180 A | 6/2000 | Yoon et al. |
| 6,270,508 B1 | 8/2001 | Klieman et al. |
| 6,322,578 B1 | 11/2001 | Houle et al. |
| 6,383,199 B2 | 5/2002 | Carter et al. |
| 6,503,264 B1 | 1/2003 | Birk |
| 6,517,552 B1 | 2/2003 | Nord et al. |
| 6,554,829 B2 | 4/2003 | Schulze et al. |
| 6,616,683 B1 | 9/2003 | Toth et al. |
| 6,629,984 B1 | 10/2003 | Chan |
| 6,676,673 B2 | 1/2004 | Chang |
| 6,716,224 B2 | 4/2004 | Singhatat |
| 6,723,107 B1 | 4/2004 | Skiba et al. |
| 6,770,084 B1 | 8/2004 | Bain et al. |
| 6,840,900 B2 | 1/2005 | Smith |
| 6,921,408 B2 | 7/2005 | Sauer |
| 6,936,054 B2 | 8/2005 | Chu |
| 6,945,984 B2 | 9/2005 | Arumi et al. |
| 6,991,636 B2 | 1/2006 | Rose |
| 7,033,315 B2 | 4/2006 | Smith |
| 7,063,699 B2 | 6/2006 | Hess et al. |
| 7,105,000 B2 | 9/2006 | McBrayer |
| 7,105,004 B2 | 9/2006 | Dicesare et al. |
| 7,131,978 B2 | 11/2006 | Sancoff et al. |
| 7,137,988 B2 | 11/2006 | Frye |
| 7,147,650 B2 | 12/2006 | Lee |
| 7,169,156 B2 | 1/2007 | Hart |
| 7,261,725 B2 | 8/2007 | Binmoeller |
| 7,338,513 B2 | 3/2008 | Lee et al. |
| 7,364,582 B2 | 4/2008 | Lee |
| 7,736,372 B2 | 6/2010 | Reydel et al. |
| 7,766,937 B2 | 8/2010 | Ravikumar |
| 7,815,654 B2 | 10/2010 | Chu |
| 7,842,050 B2 | 11/2010 | Diduch et al. |
| 7,879,048 B2 | 2/2011 | Bain et al. |
| 7,883,519 B2 | 2/2011 | Oren et al. |
| 8,066,718 B2 | 11/2011 | Weisel et al. |
| 8,105,350 B2 | 1/2012 | Lee et al. |
| 8,133,255 B2 | 3/2012 | Ravikumar |
| 8,157,817 B2 | 4/2012 | Bonadio et al. |
| 8,230,863 B2 | 7/2012 | Ravikumar et al. |
| 8,308,725 B2 | 11/2012 | Bell et al. |
| 8,313,507 B2 | 11/2012 | Ravikumar |
| 8,328,824 B2 | 12/2012 | Hart |
| 8,361,089 B2 | 1/2013 | Chu |
| 8,469,992 B2 | 6/2013 | Roy et al. |
| 8,545,521 B2 | 10/2013 | McClurg et al. |

(56) References Cited

U.S. PATENT DOCUMENTS

| | | |
|---|---|---|
| 8,556,916 B2 | 10/2013 | Torrie |
| 8,585,714 B2 | 11/2013 | Weisel et al. |
| 8,679,135 B2 | 3/2014 | Stone et al. |
| 8,758,368 B2 | 6/2014 | Weisel et al. |
| 8,758,405 B2 | 6/2014 | Zeiner et al. |
| 8,870,897 B2 | 10/2014 | Torrie |
| 8,906,041 B2 | 12/2014 | Chu |
| 9,066,717 B2 | 6/2015 | Sherts et al. |
| 9,089,323 B2 | 7/2015 | Bonutti et al. |
| 2003/0171760 A1 | 9/2003 | Gambale |
| 2004/0236353 A1 | 11/2004 | Bain et al. |
| 2004/0249393 A1 | 12/2004 | Weisel et al. |
| 2006/0069399 A1 | 3/2006 | Weisel et al. |
| 2006/0069699 A1 | 3/2006 | Smadja et al. |
| 2007/0118153 A1 | 5/2007 | Funamura et al. |
| 2007/0185505 A1 | 8/2007 | Hart |
| 2007/0250112 A1 | 10/2007 | Ravikumar et al. |
| 2009/0062743 A1 | 3/2009 | Rotella et al. |
| 2010/0016884 A1 | 1/2010 | Ravikumar |
| 2010/0198235 A1 | 8/2010 | Pierce et al. |
| 2010/0292724 A1 | 11/2010 | Ravikumar et al. |
| 2011/0066165 A1 | 3/2011 | Skinlo et al. |
| 2011/0071550 A1 | 3/2011 | Diduch et al. |
| 2011/0106124 A1 | 5/2011 | Beauchamp |
| 2011/0270280 A1 | 11/2011 | Saliman |
| 2012/0123448 A1 | 5/2012 | Flom et al. |
| 2012/0172897 A1 | 7/2012 | McClurg et al. |
| 2013/0116709 A1 | 5/2013 | Ziniti et al. |
| 2013/0211415 A1 | 8/2013 | Zerfas et al. |
| 2013/0218173 A1 | 8/2013 | Weisel et al. |
| 2013/0218175 A1 | 8/2013 | Auerbach et al. |
| 2013/0226200 A1 | 8/2013 | Kappel et al. |
| 2013/0253542 A1 | 9/2013 | Ostrovsky et al. |
| 2013/0253543 A1 | 9/2013 | Heneveld |
| 2014/0012292 A1 | 1/2014 | Stewart et al. |
| 2014/0039529 A1 | 2/2014 | Torrie |
| 2014/0039530 A1 | 2/2014 | Torrie |
| 2014/0188138 A1 | 7/2014 | Melsheimer et al. |
| 2014/0207158 A1 | 7/2014 | Stone et al. |
| 2014/0222033 A1 | 8/2014 | Foerster et al. |
| 2014/0228865 A1 | 8/2014 | Weisel et al. |
| 2014/0303653 A1 | 10/2014 | Weisel et al. |
| 2015/0018854 A1 | 1/2015 | Haines et al. |
| 2015/0025550 A1 | 1/2015 | Heneveld |
| 2015/0051622 A1 | 2/2015 | Domingo |
| 2015/0088167 A1 | 3/2015 | Chin et al. |
| 2015/0094739 A1 | 4/2015 | Norton et al. |
| 2015/0100073 A1 | 4/2015 | Chu |
| 2015/0112368 A1 | 4/2015 | Stewart et al. |
| 2015/0157317 A1 | 6/2015 | Bagaoisan et al. |
| 2015/0282804 A1 | 10/2015 | Bonutti et al. |

FOREIGN PATENT DOCUMENTS

| | | |
|---|---|---|
| WO | WO 97/03615 | 2/1997 |
| WO | WO 2012/034131 | 3/2012 |
| WO | WO 2012/093094 | 7/2012 |

OTHER PUBLICATIONS

Caborn, D. et al., "Arthroscopic Repair of a Bankhart Lesion Using Tag® Suture Anchors", Andover, MA, Smith & Nephew Endoscopy, 1996.

METHOD AND APPARATUS FOR PASSING SUTURE THROUGH TISSUE

REFERENCE TO PENDING PRIOR PATENT APPLICATIONS

This patent application claims benefit of:

(i) pending prior U.S. Provisional Patent Application Ser. No. 61/384,423, filed Sep. 20, 2010 by Chris Pamichev et al. for METHOD AND APPARATUS FOR PASSING SUTURE THROUGH TISSUE DURING AN ARTHROSCOPIC PROCEDURE, INCLUDING THE PROVISION AND USE OF A NOVEL SPEAR SUTURE PASSER;

(ii) pending prior U.S. Provisional Patent Application Ser. No. 61/473,219, filed Apr. 8, 2011 by James Flom et al. for METHOD AND APPARATUS FOR PASSING SUTURE THROUGH TISSUE;

(iii) pending prior U.S. Provisional Patent Application Ser. No. 61/495,441, filed Jun. 10, 2011 by James Flom et al. for METHOD AND APPARATUS FOR PASSING SUTURE THROUGH TISSUE; and (iv) pending prior U.S. Provisional Patent Application Ser. No. 61/381,787, filed Sep. 10, 2010 by Thomas Weisel for PINCH PASSER.

The four (4) above-identified patent applications are hereby incorporated herein by reference.

FIELD OF THE INVENTION

This invention relates to surgical apparatus and procedures in general, and more particularly to surgical apparatus and procedures for passing suture through tissue.

BACKGROUND OF THE INVENTION

In many situations suture must be passed through tissue. In open surgical procedures, the suture is typically attached to a needle and the needle is then used to draw the suture through the tissue. However, in closed surgical procedures (e.g., so-called "keyhole" surgeries, where an interior surgical site is accessed through a narrow cannula), it can be difficult to advance a needle (and particularly a curved needle) to the interior surgical site, and it can be even more difficult to maneuver the needle about the interior surgical site. Furthermore, in closed surgical procedures, it is frequently necessary to advance the suture through tissue, and then to retrieve the suture on the far side of the tissue, so that the suture can thereafter be drawn back through the tissue, e.g., at a second point of penetration. Conventional needles are typically inadequate for these situations.

On account of the foregoing, in closed surgical procedures, it is common to use a suture passer to pass suture through tissue, e.g., at a remote surgical site. However, such suture passers all tend to suffer from one or more deficiencies, including but not limited to: (i) size; (ii) a need to place the suture adjacent to an edge of the tissue; (iii) difficulty in picking up suture on the far side of the tissue; (iv) complexity of operation; (v) cost of manufacture, etc.

Thus there is a need for a new and improved method and apparatus for passing suture through tissue which does not suffer from one or more of the disadvantages associated with the prior art.

SUMMARY OF THE INVENTION

The present invention provides a new and improved method and apparatus for passing suture through tissue.

In one form of the present invention, there is provided a suture passer comprising:

a hollow tube, the hollow tube comprising a distal end, a proximal end, a lumen extending from the distal end to the proximal end, and a window formed in the sidewall of the hollow tube, the window communicating with the lumen; and a clamping rod slidably received in the lumen of the hollow tube, the clamping rod comprising a distal end and a proximal end, the distal end being bifurcated into a first arm and a second arm, one of the first and second arms extending distally of the other of the first and second arms and including a clamping surface, and at least one of the first and second arms being outwardly biased such that when the clamping rod is moved distally so that the distal end of the at least one outwardly biased arm is adjacent to the window, the distal end of the at least one outwardly biased arm extends outwardly through the window.

In another form of the present invention, there is provided a method for passing suture through an object, the method comprising:

providing a suture passer comprising:
  a hollow tube, the hollow tube comprising a distal end, a proximal end, a lumen extending from the distal end to the proximal end, and a window formed in the sidewall of the hollow tube, the window communicating with the lumen; and
  a clamping rod slidably received in the lumen of the hollow tube, the clamping rod comprising a distal end and a proximal end, the distal end being bifurcated into a first arm and a second arm, one of the first and second arms extending distally of the other of the first and second arms and including a clamping surface, and at least one of the first and second arms being outwardly biased such that when the clamping rod is moved distally so that the distal end of the at least one outwardly biased arm is adjacent to the window, the distal end of the at least one outwardly biased arm extends outwardly through the window;

positioning the clamping rod so that the at least one outwardly biased arm extends out of the window;

positioning at least one of the suture passer and the suture so that the suture is disposed in the window;

moving the clamping rod proximally so that the clamping surface clamps the suture to the hollow tube; and moving the suture passer so that the suture is passed through the object.

In another form of the present invention, there is provided a suture passer comprising:

a hollow tube, the hollow tube comprising a pointed distal end, a proximal end and a lumen extending from the distal end to the proximal end; and a clamping rod slidably received in the lumen of the hollow tube, the clamping rod comprising a distal end and a proximal end, the distal end being bifurcated into a first arm and a second arm, the first arm extending distally of the second arm and including a clamping surface, and the second arm being outwardly biased such that when the clamping rod is moved distally so that the distal end of the second arm extends out of the distal end of the hollow tube, the distal end of the second arm extends laterally of the hollow tube.

In another form of the present invention, there is provided a method for passing suture through an object, the method comprising:

providing a suture passer comprising:

a hollow tube, the hollow tube comprising a pointed distal end, a proximal end and a lumen extending from the distal end to the proximal end; and a clamping rod slidably received in the lumen of the hollow tube, the clamping rod comprising a distal end and a proximal end, the distal end being bifurcated into a first arm and a second arm, the first arm extending distally of the second arm and including a clamping surface, and the second arm being outwardly biased such that when the clamping rod is moved distally so that the distal end of the second arm extends out of the distal end of the hollow tube, the distal end of the second arm extends laterally of the hollow tube;

positioning the clamping rod so that the second arm extends out of the distal end of the hollow tube;

positioning at least one of the suture passer and the suture so that the suture is disposed between the clamping surface and the distal end of the hollow tube;

moving the clamping rod proximally so that the clamping surface clamps the suture to the hollow tube; and moving the suture passer so that the suture is passed through the object.

In another form of the present invention, there is provided a suture passer comprising:

a shaft comprising a distal end, a proximal end, a lumen extending from the proximal end toward the distal end, and a window formed in the sidewall of the shaft, the window communicating with the lumen; and a suture spear movable within the lumen of the shaft, the suture spear comprising a distal end and a proximal end, the distal end being pointed to pierce a suture located in the window.

In another form of the present invention, there is provided a method for passing suture through an object, the method comprising:

providing a suture passer comprising:

a shaft comprising a distal end, a proximal end, a lumen extending from the proximal end toward the distal end, and a window formed in the sidewall of the shaft, the window communicating with the lumen; and a suture spear movable within the lumen of the shaft, the suture spear comprising a distal end and a proximal end, the distal end being pointed to pierce a suture located in the window.

positioning the suture spear so that it is disposed proximal to the window;

positioning at least one of the suture passer and the suture so that the suture is disposed in the window;

moving the suture spear distally so that the suture spear extends into the suture disposed in the window; and moving the suture passer so that the suture is passed through the object.

In another form of the present invention, there is provided a suture passer comprising:

a hollow tube, the hollow tube comprising a distal end, a proximal end, a lumen extending from the distal end to the proximal end, and a window formed in the sidewall of the hollow tube, the window communicating with the lumen; and a clamping rod slidably received in the lumen of the hollow tube, the clamping rod comprising a distal end and a proximal end, the distal end including a clamping surface, and the distal end being outwardly biased such that when the clamping rod is moved distally so that the distal end of the clamping rod is adjacent to the window, the distal end of the clamping rod extends outwardly through the window.

In another form of the present invention, there is provided a method for passing suture through an object, the method comprising:

providing a suture passer comprising:

a hollow tube, the hollow tube comprising a distal end, a proximal end, a lumen extending from the distal end to the proximal end, and a window formed in the sidewall of the hollow tube, the window communicating with the lumen; and a clamping rod slidably received in the lumen of the hollow tube, the clamping rod comprising a distal end and a proximal end, the distal end including a clamping surface, and the distal end being outwardly biased such that when the clamping rod is moved distally so that the distal end of the clamping rod is adjacent to the window, the distal end of the clamping rod extends outwardly through the window;

positioning the clamping rod so that the distal end of the clamping rod extends out of the window;

positioning at least one of the suture passer and the suture so that the suture is disposed in the window;

moving the clamping rod proximally so that the clamping surface clamps the suture to the hollow tube; and moving the suture passer so that the suture is passed through the object.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
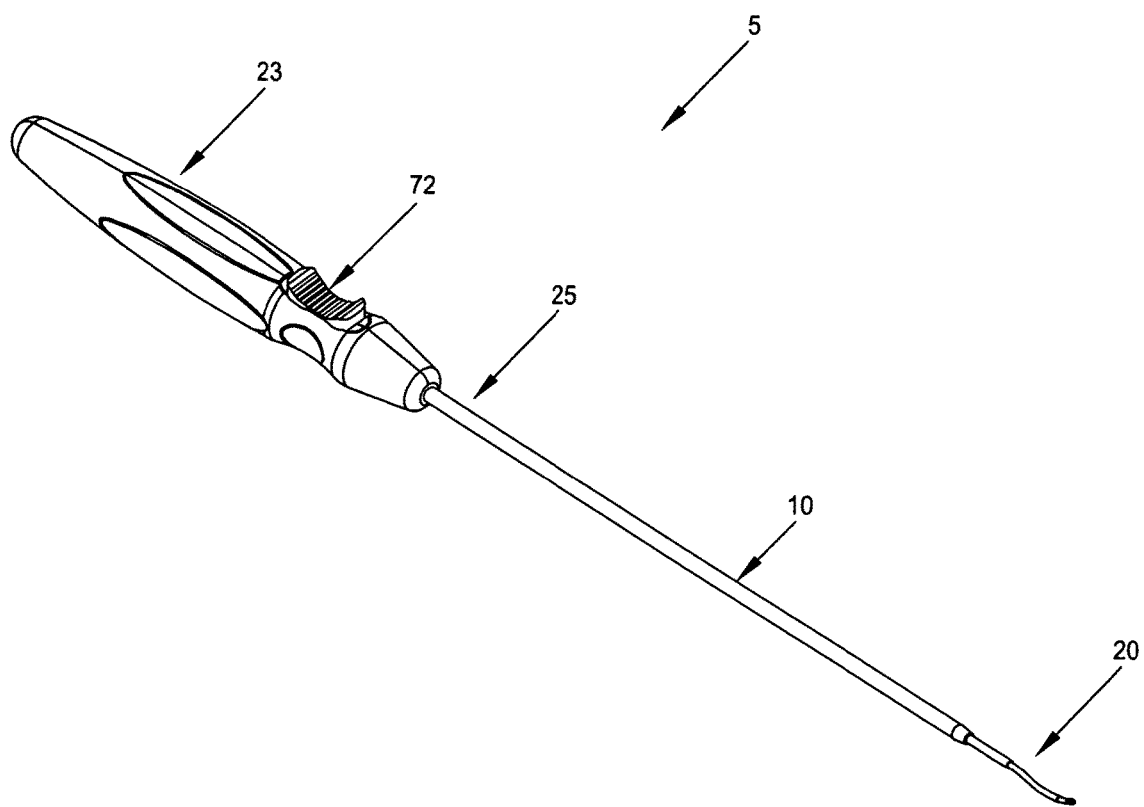
FIGS. 1-11 are schematic views showing a novel suture passer formed in accordance with the present invention.
Figure 2:
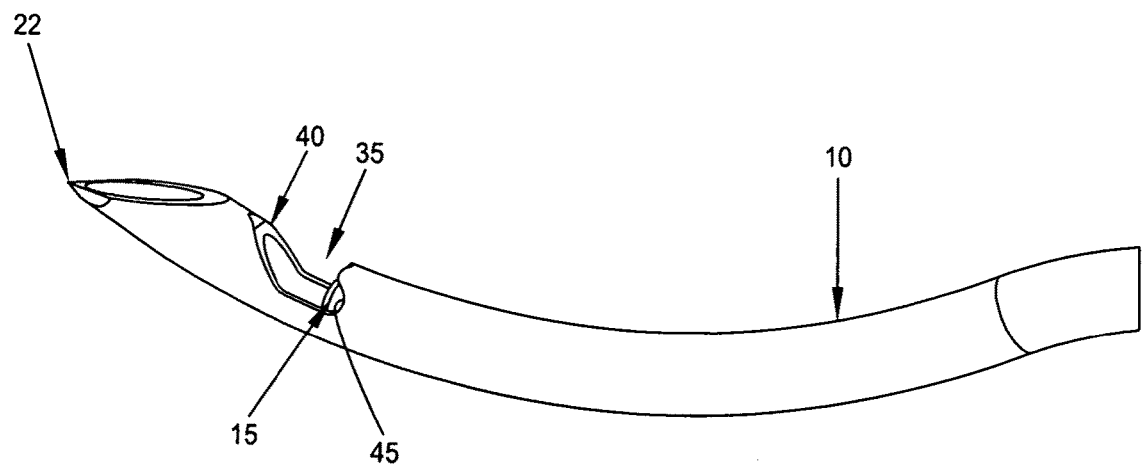
Figure 3:
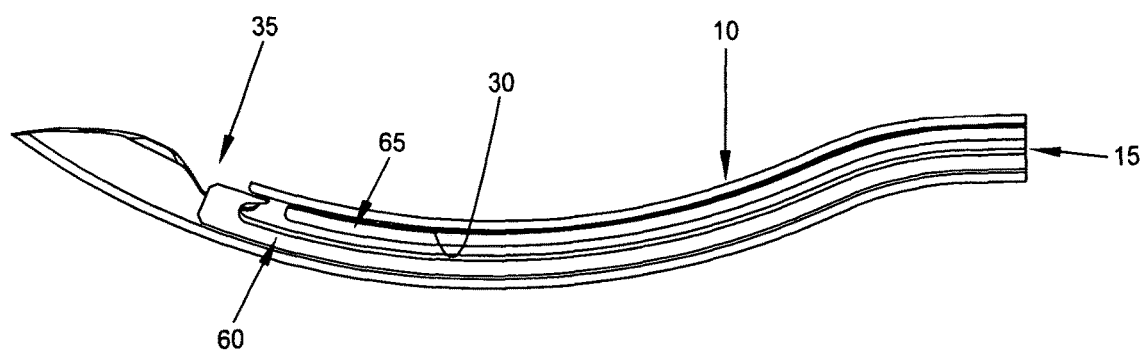
Figure 4:
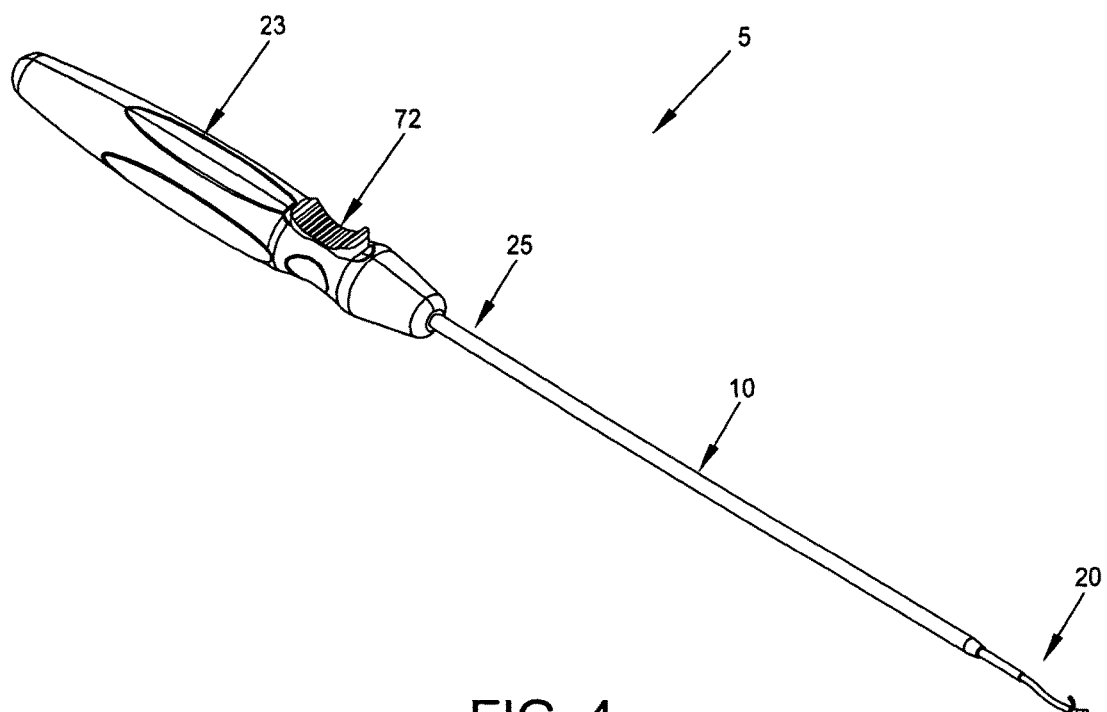

The present invention provides a new and improved method and apparatus for passing suture through tissue.

The Novel Suture Passer

Looking first at FIGS. 1-11, there is shown a novel suture passer 5 formed in accordance with the present invention. Suture passer 5 generally comprises a hollow tube 10 and a clamping rod 15 slidably disposed within the lumen of hollow tube 10, as will hereinafter be discussed in further detail.

More particularly, hollow tube 10 comprises a distal end 20 preferably terminating in a sharp point 22, and a proximal end 25 preferably terminating in a handle 23, with a lumen 30 extending therebetween. It will be appreciated that the pointed hollow tube 10 essentially comprises a hollow needle adapted to pierce tissue.

Hollow tube 10 further comprises a window 35 which extends radially into the hollow tube and communicates with lumen 30. Window 35 is sized so as to selectively receive a suture S therein, as will hereinafter be discussed in further detail. Window 35 preferably comprises an inclined distal surface 40 and an inclined proximal surface 45. Preferably, distal surface 40 and proximal surface 45 are inclined in the same direction, and preferably both surfaces are inclined distally (e.g., in the manner shown in FIGS. 1-11). The forward incline of inclined distal surface 40 allows suture to more easily pass into and out of window 35. The forward incline of inclined proximal surface 45 provides an undercut which helps to trap the suture S between the clamping surface 47 of clamping rod 15 and the inclined proximal surface 45 of window 35, as will hereinafter be discussed in further detail.

Hollow tube 10 is preferably formed out of a substantially rigid material (e.g., stainless steel) so as to maintain rigidity when passing through tissue, particularly relatively tough fibrous tissue (e.g., the labrum of the hip).

In one preferred form of the present invention, the distal end 20 of hollow tube 10 is curved, however, it should be appreciated that hollow tube 10 can be formed in other configurations well known in the art (e.g., straight, etc.).

Figure 9:
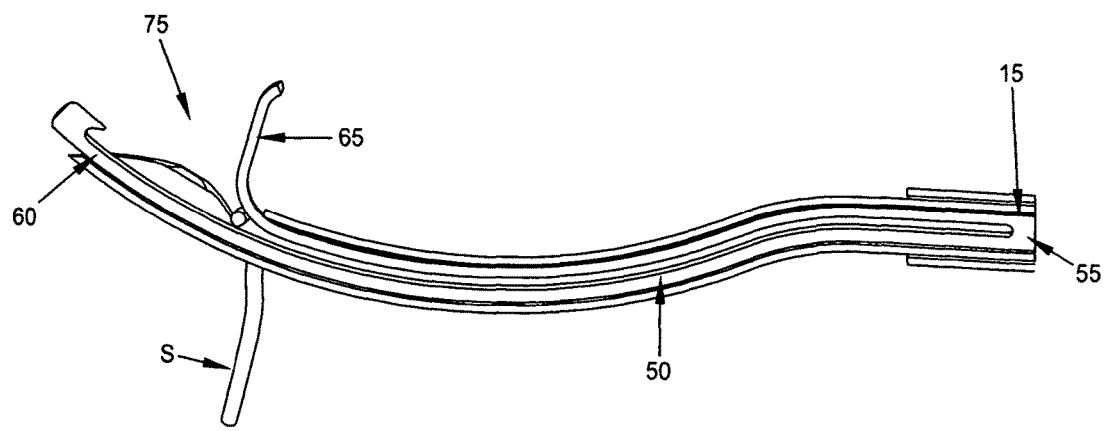

Clamping rod 15 comprises a distal end 50 (FIG. 9) and a proximal end 55 (FIG. 9). Distal end 50 of clamping rod 15 is bifurcated so as to form a first arm 60 and a second arm 65.

First arm 60 comprises the aforementioned clamping surface 47, with clamping surface 47 extending radially from the longitudinal axis of clamping rod 15. Clamping surface 47 may take the form of a hook, as shown in FIGS. 1-11. This hook helps trap the suture S between clamping surface 47 of clamping rod 15 and inclined proximal surface 45 of window 35, in the manner shown in FIGS. 10 and 11.

Second arm 65 extends parallel to first arm 60 when clamping rod 15 is disposed within lumen 30 of hollow tube 10, with second arm 65 terminating proximally of first arm 60, shy of clamping surface 47.

Second arm 65 is outwardly biased so that when second arm 65 advances past window 35, second arm 65 passes radially outwardly through window 35 so as to project at an angle of approximately 10-120 degrees relative to the longitudinal axis of first arm 60 (FIG. 6), and more preferably at an angle of approximately 30-90 degrees to the longitudinal axis of first arm 60, whereby to create a funnel region 75 between hollow tube 10 and second arm 65 when second arm 65 extends out window 35. To this end, second arm 65 is preferably formed out of a material consistent with this spring bias (e.g., a superelastic material such as Nitinol, etc.). In one preferred form of the invention, the entire clamping rod 15 is formed out of a superelastic material such as Nitinol.

The proximal end 55 of clamping rod 15 extends through lumen 30 of hollow tube 10 and is connected to an actuator 72 (FIG. 1) which is movably mounted to handle 23, such that movement of actuator 72 relative to handle 23 will cause movement of clamping rod 15 relative to hollow tube 10.

Figure 5:
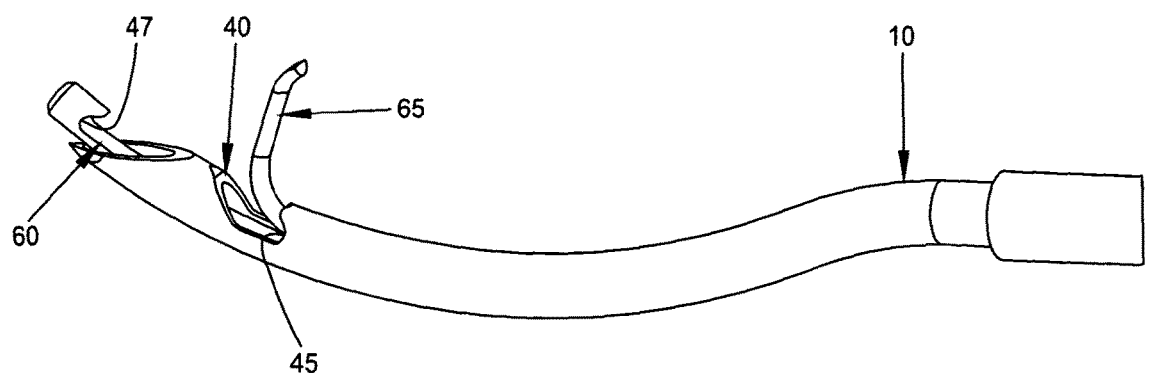
Figure 6:
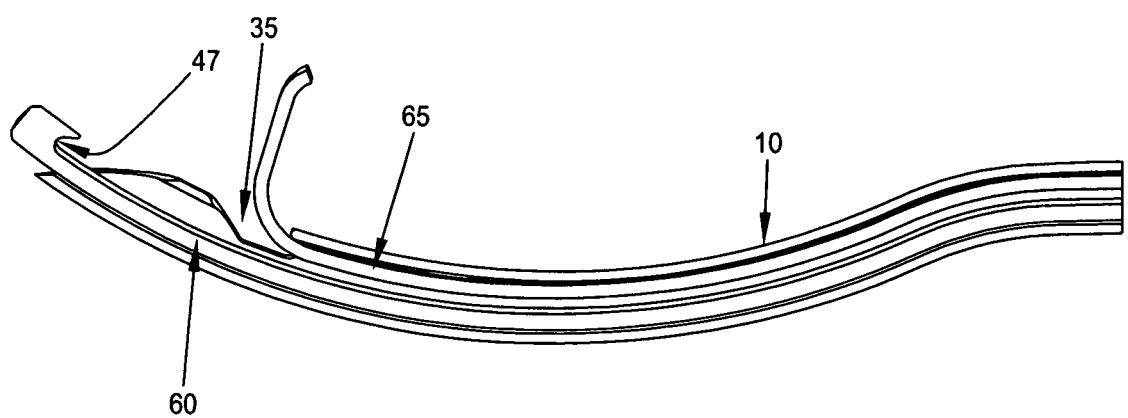
Figure 7:
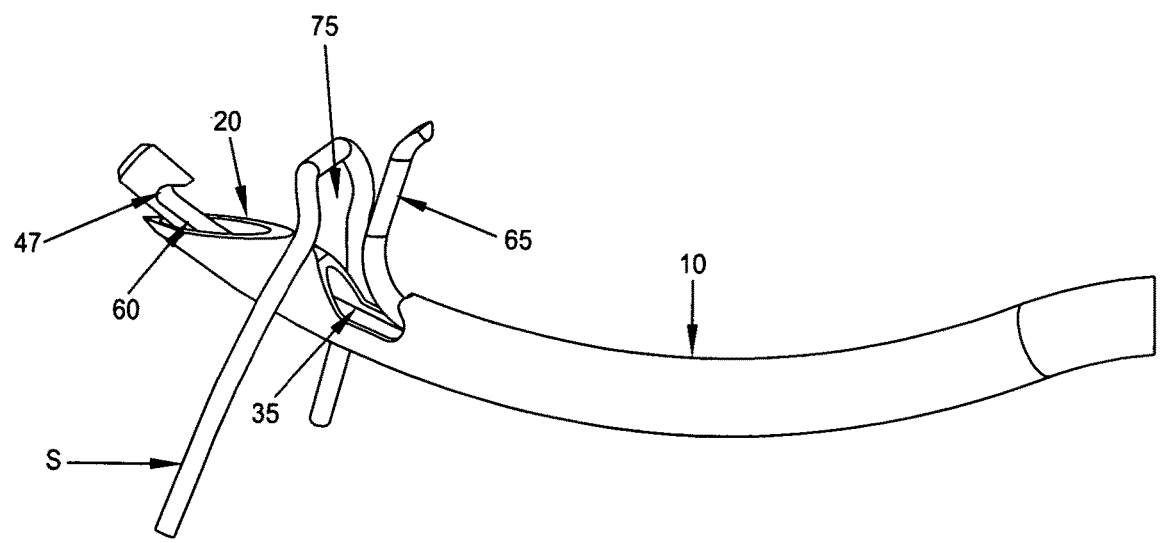
Figure 8:
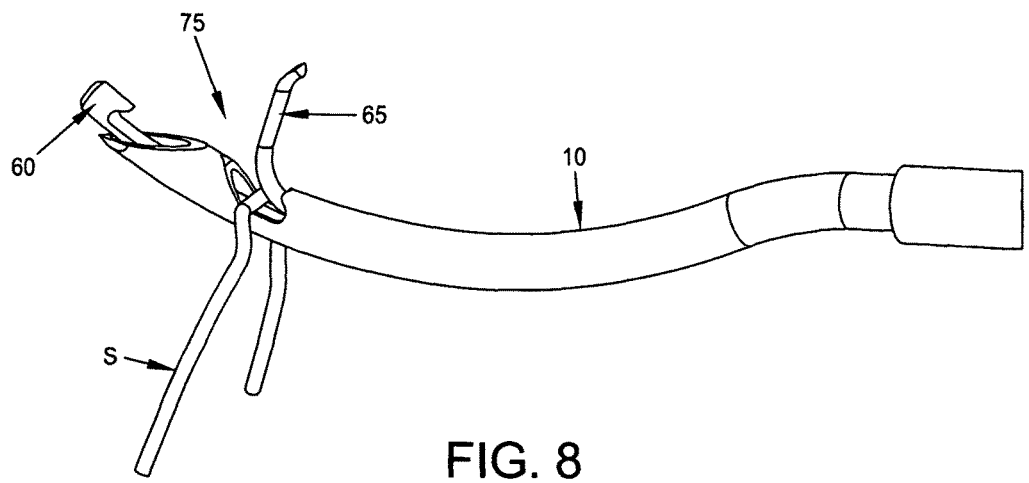
Figure 10:
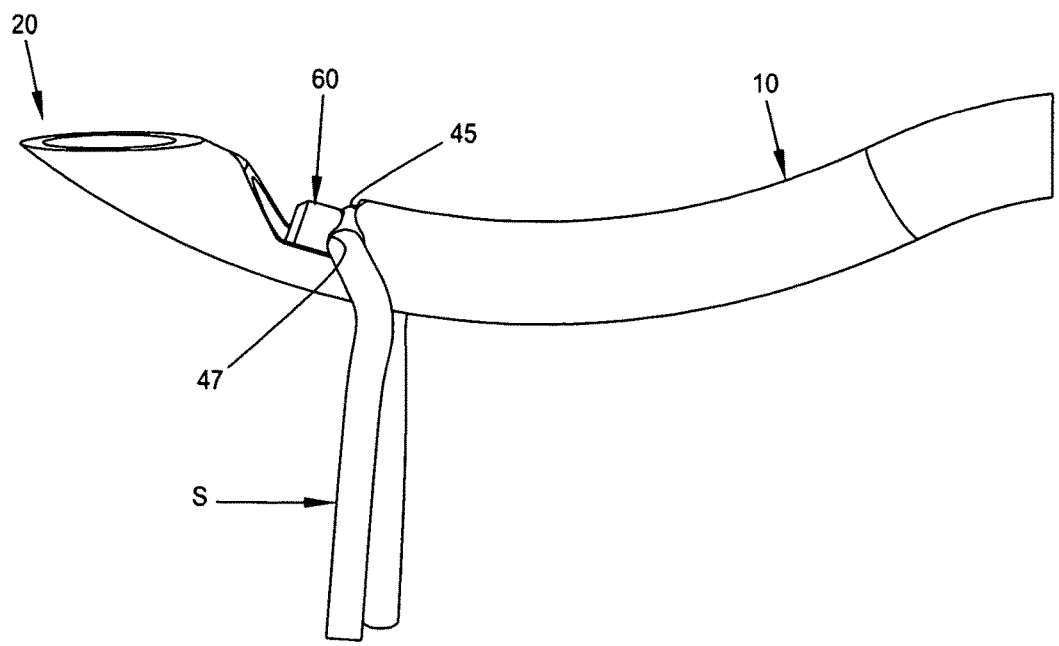
Figure 11:
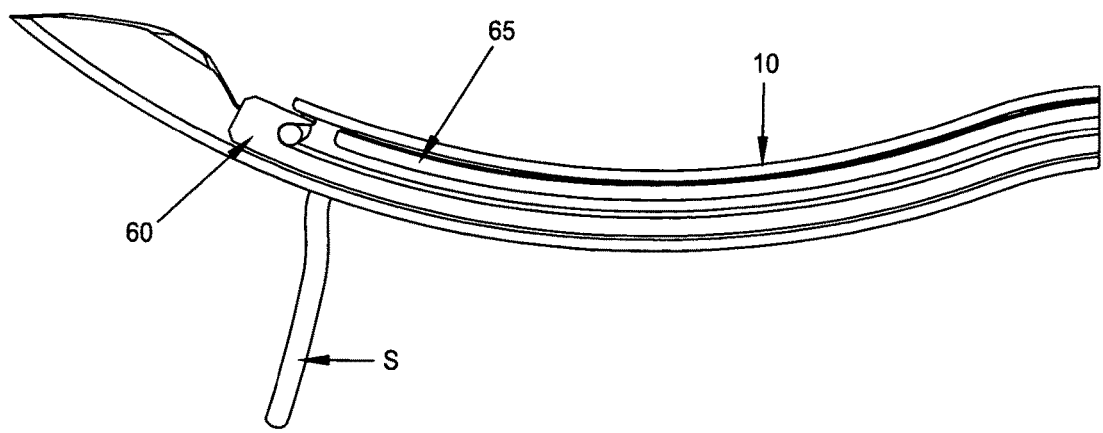

It will be appreciated that, on account of the foregoing construction, a piece of suture S may be clamped to the distal end of suture passer 5 by (i) moving clamping rod 15 to the position shown in FIGS. 5 and 6 (e.g., by moving actuator 72 distally relative to handle 23) so that clamping surface 47 of first arm 60 is distal to window 35, and so that second arm 65 extends out of window 35; (ii) positioning the suture S in window 35 (FIGS. 7-9); and (iii) moving clamping rod 15 proximally (e.g., by moving actuator 72 proximally relative to handle 23) so as to cause clamping surface 47 of first arm 60 to clamp suture S against proximal surface 45 of window 35, as shown in FIGS. 10 and 11. In this respect it will be appreciated that the creation of the funnel region 75 (established between hollow tube 10 and the extended second arm 65) at the mouth of window 35 facilitates guidance of suture S into window 35, as shown in FIGS. 7-9.

It will also be appreciated that, on account of the foregoing construction, a clamped piece of suture may thereafter be released from suture passer 5 by (a) moving clamping rod 15 distally (FIGS. 8 and 9) so as to space clamping surface 47 of first arm 60 away from proximal surface 45 of window 35; and (b) causing suture S to be withdrawn from window 35 (FIG. 7), either by moving suture S relative to suture passer 5 or by moving suture passer 5 relative to suture S or by moving both suture S and suture passer 5 relative to one another.

It should be appreciated that, in one preferred form of the invention, when clamping rod 15 is moved proximally, both first arm 60 and second arm 65 are disposed within lumen 30 of hollow tube 10, so that the distal end of suture passer 5 presents a smooth outer surface, whereby to facilitate passage of the distal end of suture passer 5 through tissue.

Using the Novel Suture Passer to Pass Suture from the Near Side of Tissue to the Far Side of Tissue In one preferred form of the present invention, and looking now at FIGS. 12-18, the novel suture passer 5 can be used to pass suture S from the near side of tissue T to the far side of tissue T (i.e., in an "antegrade" manner).

Figure 12:
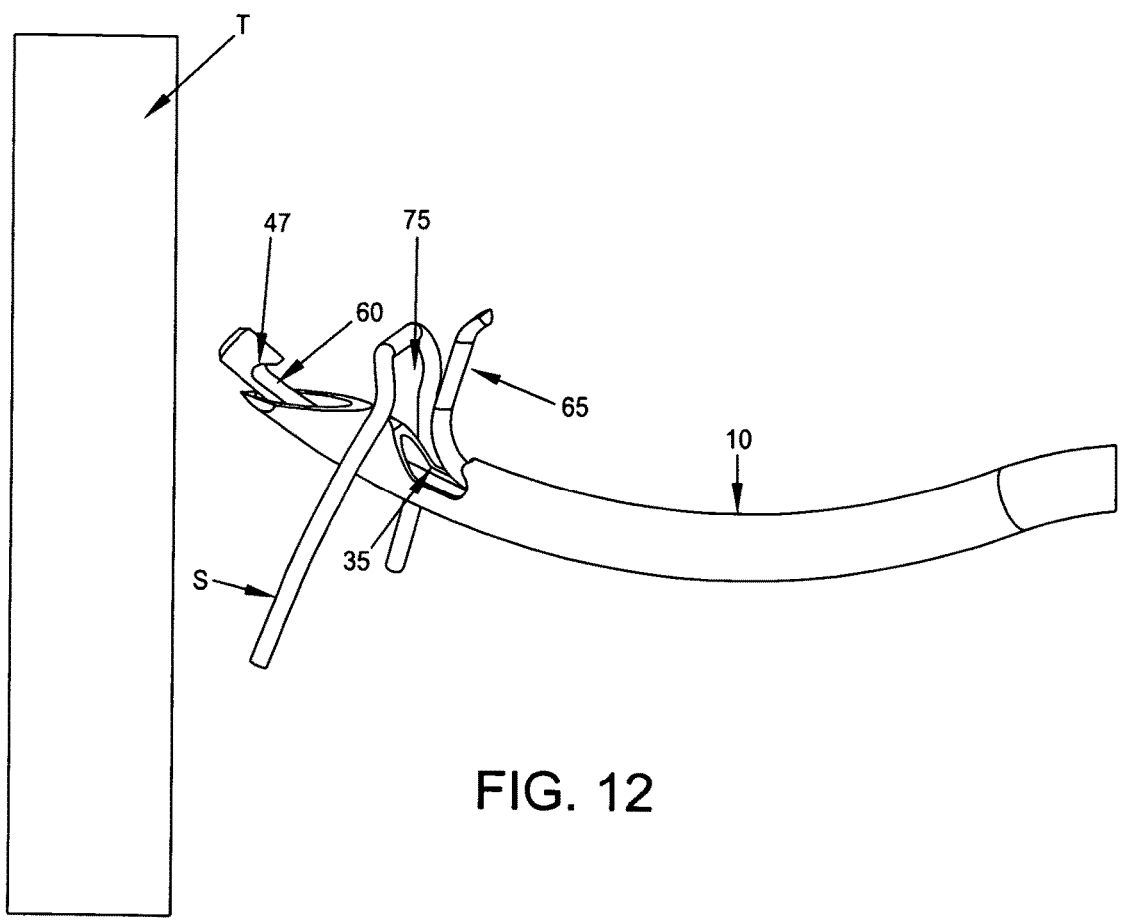
FIGS. 12-25 are schematic views showing an exemplary manner of passing suture using the novel suture passer of FIGS. 1-11.
Figure 13:
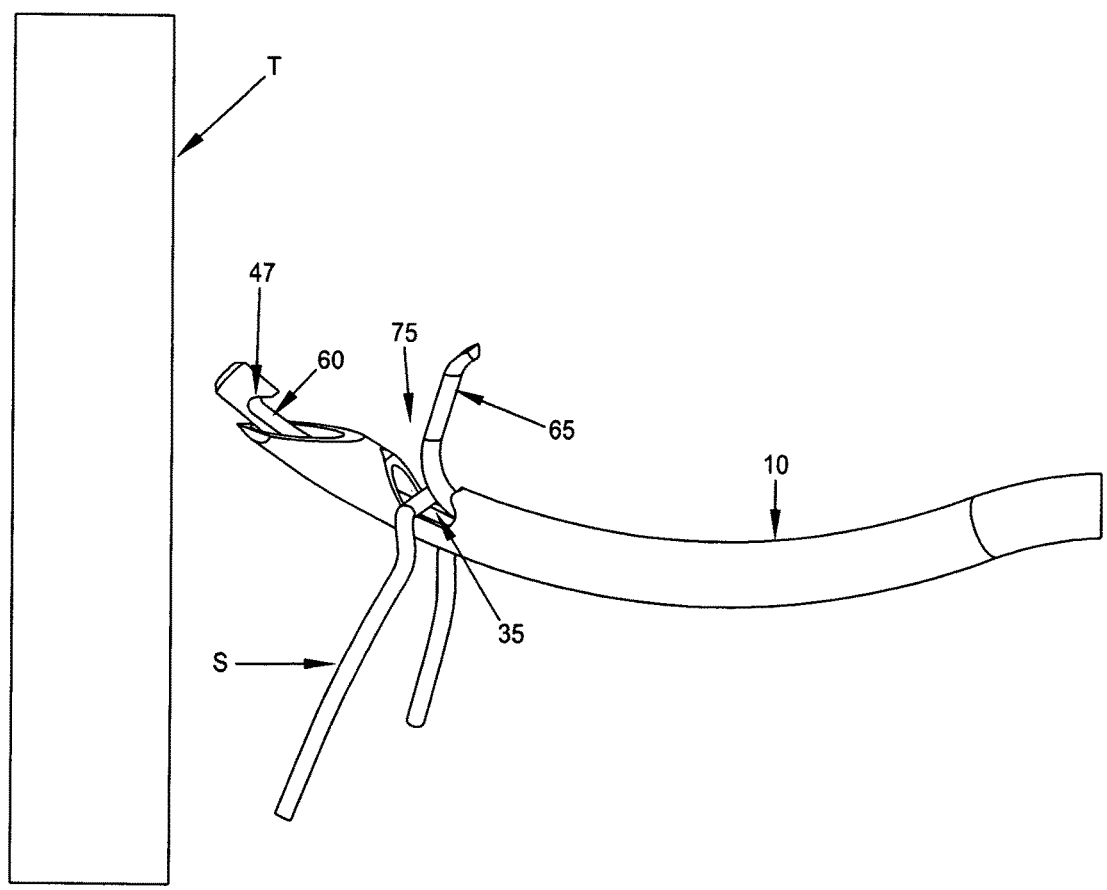
Figure 14:
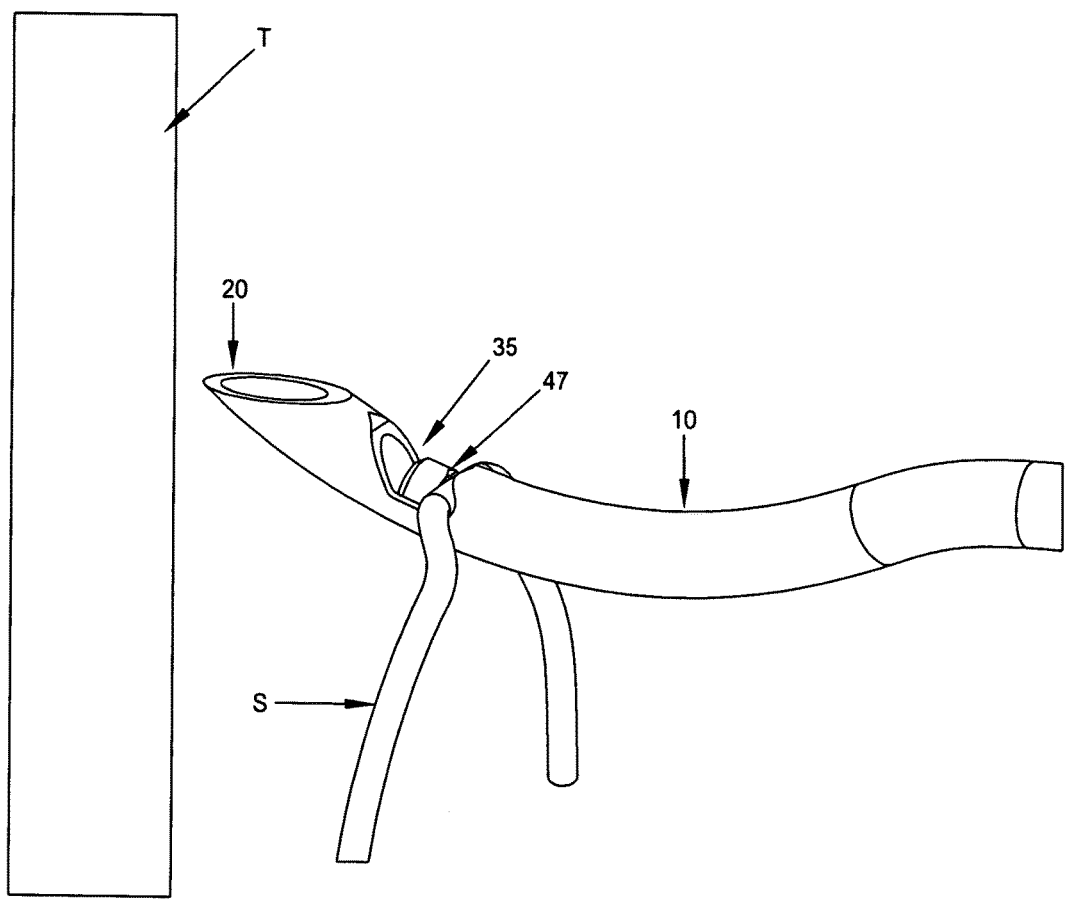

More particularly, the preliminary loading of suture S into suture passer 5 may be performed away from the surgical site (e.g., outside of the patient) or it may be performed adjacent to the near side of the tissue T which is to be sutured (e.g., inside of the patient). As seen in FIG. 12, clamping rod 15 is advanced to its most distal position so that second arm 65 advances out of window 35, whereby to project out of the axis of hollow tube 10 and create the aforementioned funnel region 75. Suture S is then guided into window 35 using this funnel effect, as seen in FIG. 13, either by moving suture S relative to suture passer 5 or by moving suture passer 5 relative to suture S or by moving both suture S and suture passer 5 relative to one another. Clamping rod 15 is then retracted proximally so that clamping surface 47 clamps suture S between clamping surface 47 of first arm 60 and proximal surface 45 of window 35. See FIG. 14.

Figure 15:
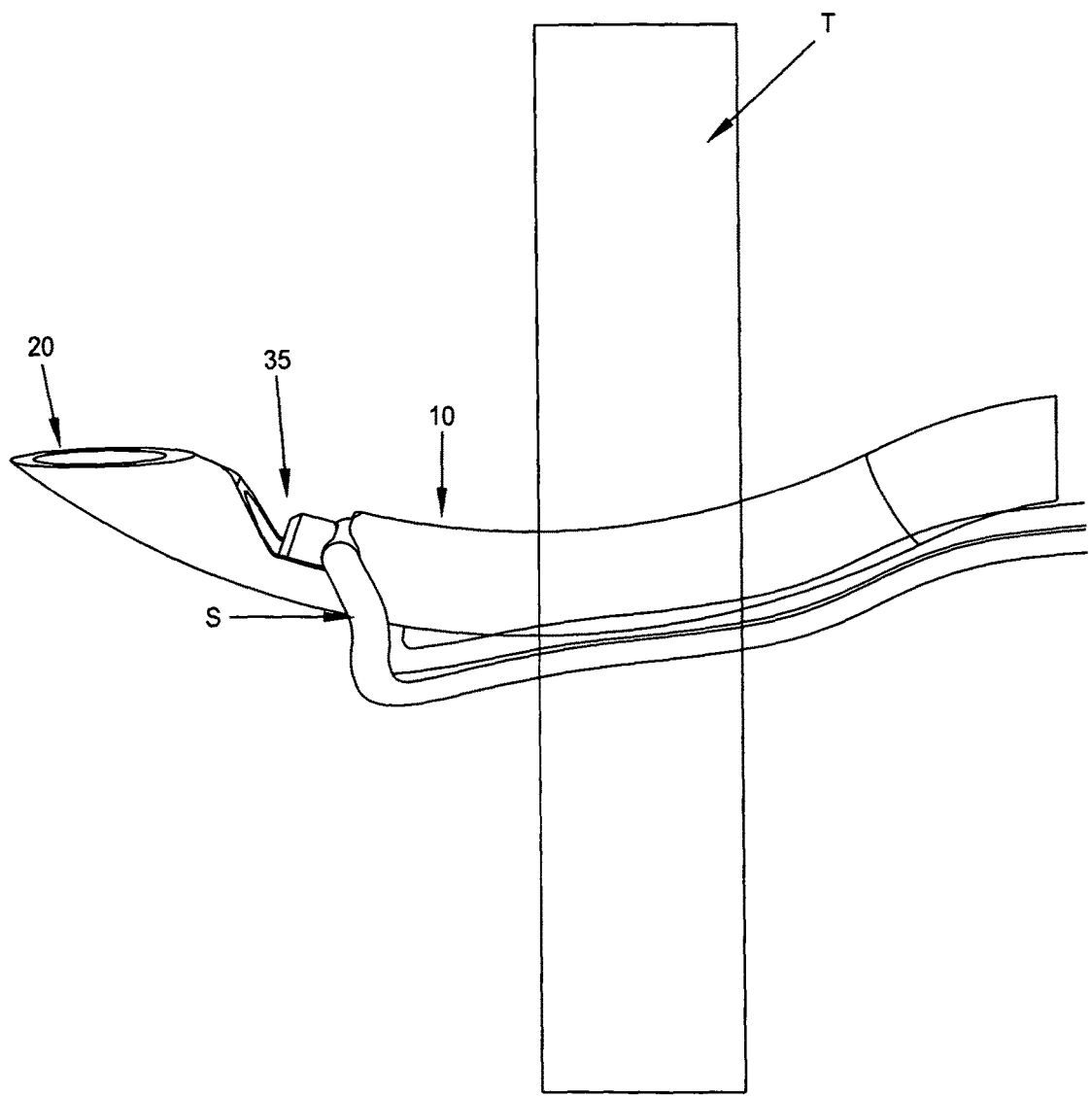
Figure 16:
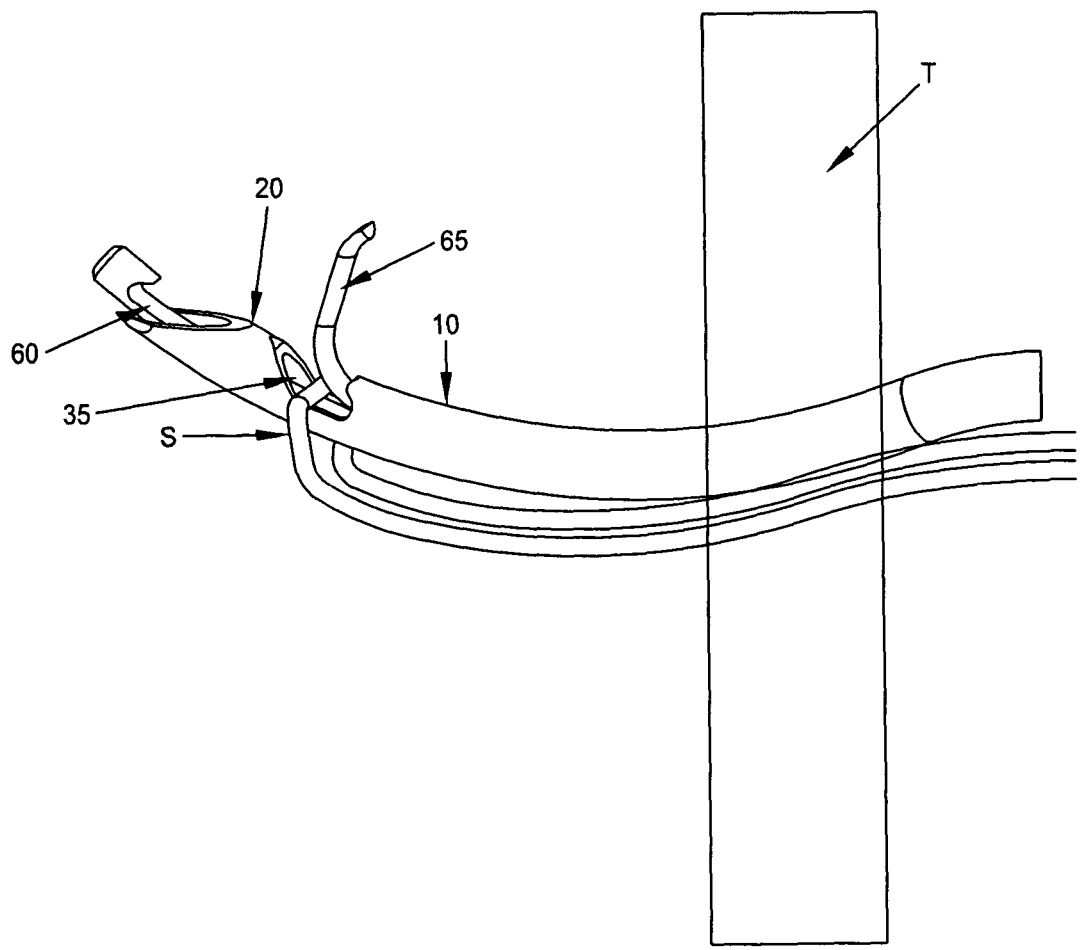
Figure 17:
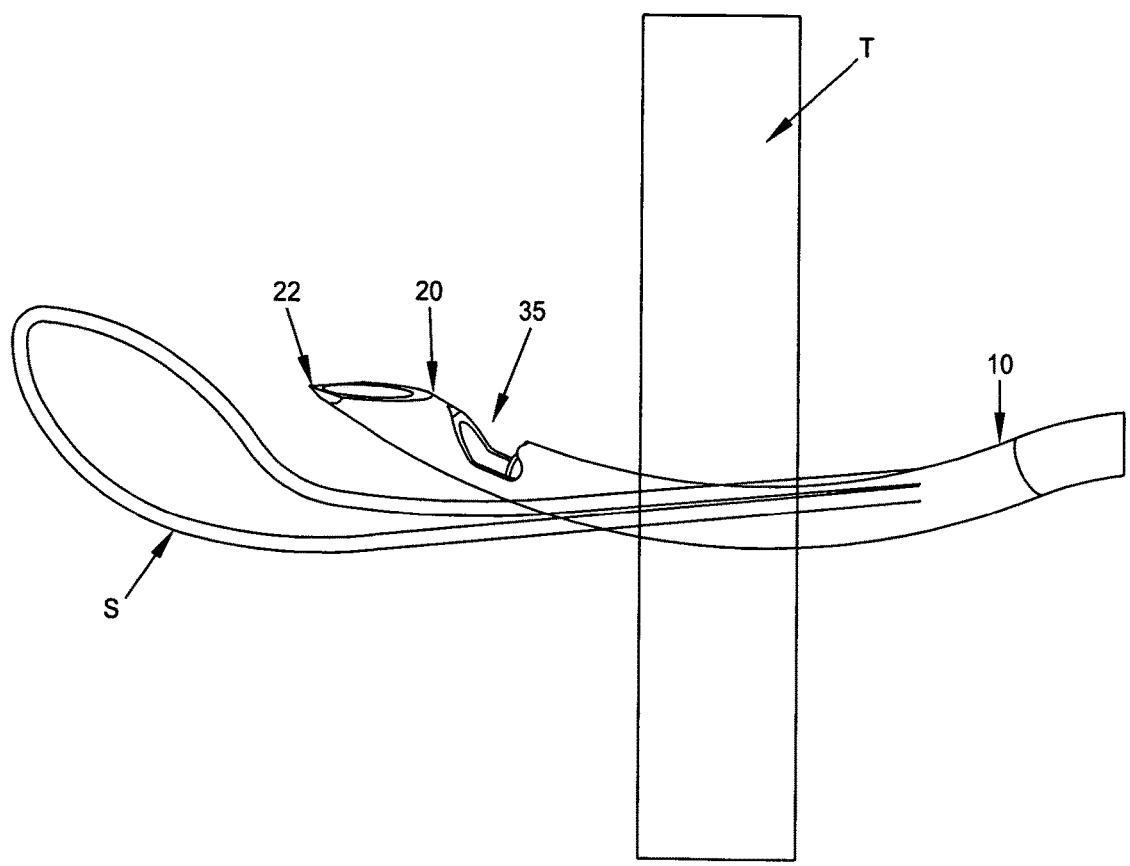
Figure 18:
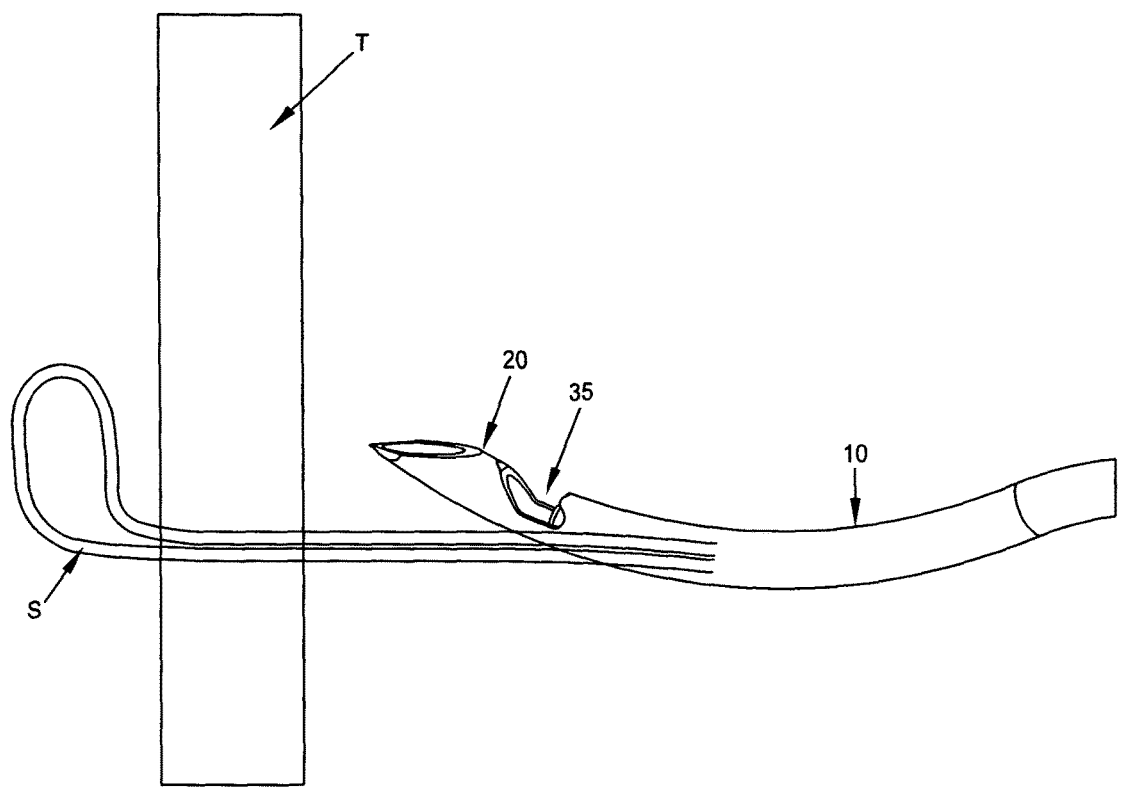

Suture passer 5 is then advanced distally so that window 35 passes through tissue T, whereby to carry suture S through the tissue (FIG. 15). With suture S extending through tissue T, and looking now at FIG. 16, clamping rod 15 is advanced distally so that clamping surface 47 is disposed distal to window 35, thereby releasing suture S from suture passer 5. Suture passer 5 and/or suture S are then manipulated so that suture S is clear of window 35 (FIG. 17). Clamping rod 15 is then moved proximally so as to retract first arm 60 and second arm 65 back into hollow tube 10. Suture passer 5 may then be withdrawn back through tissue T, leaving suture S extending through tissue T, as shown in FIG. 18.

Using the Novel Suture Passer to Draw Suture from the Far Side of Tissue to the Near Side of Tissue In another preferred form of the present invention, and looking now at FIGS. 19-25, the novel suture passer 5 can be used to draw suture S from the far side of tissue T to the near side of tissue T (i.e., in a "retrograde" manner).

Figure 19:
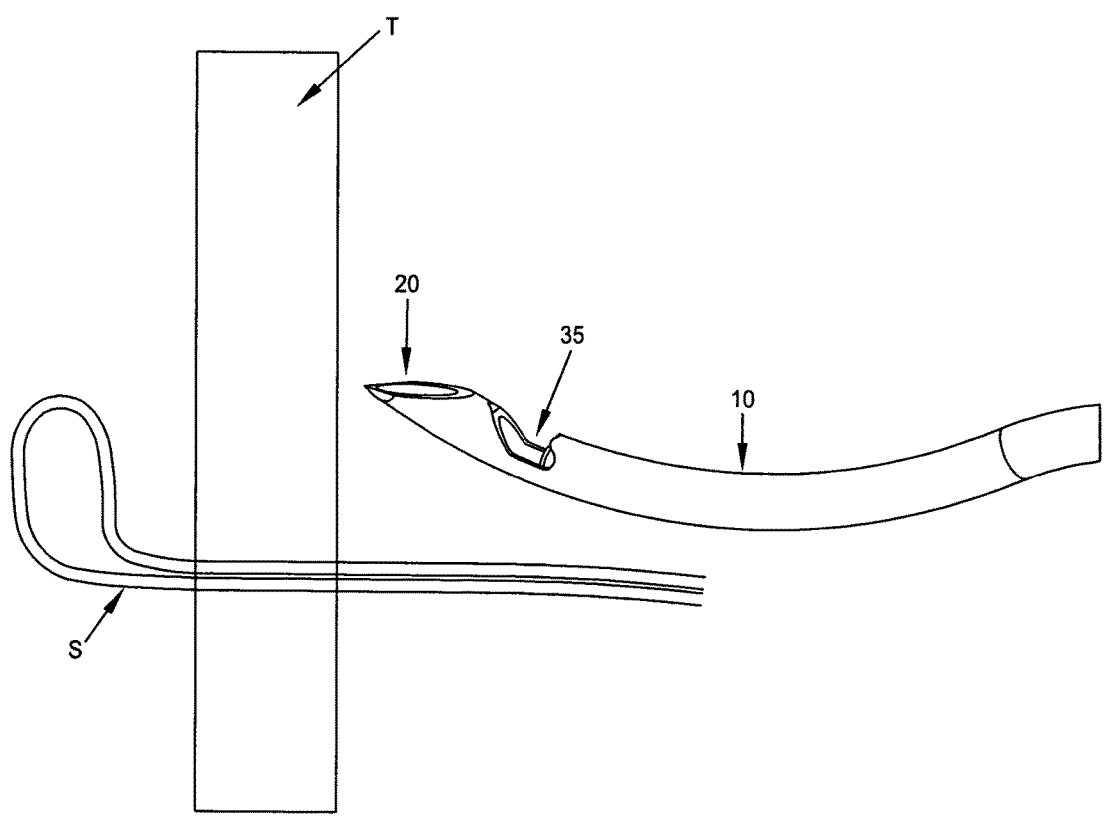
Figure 20:
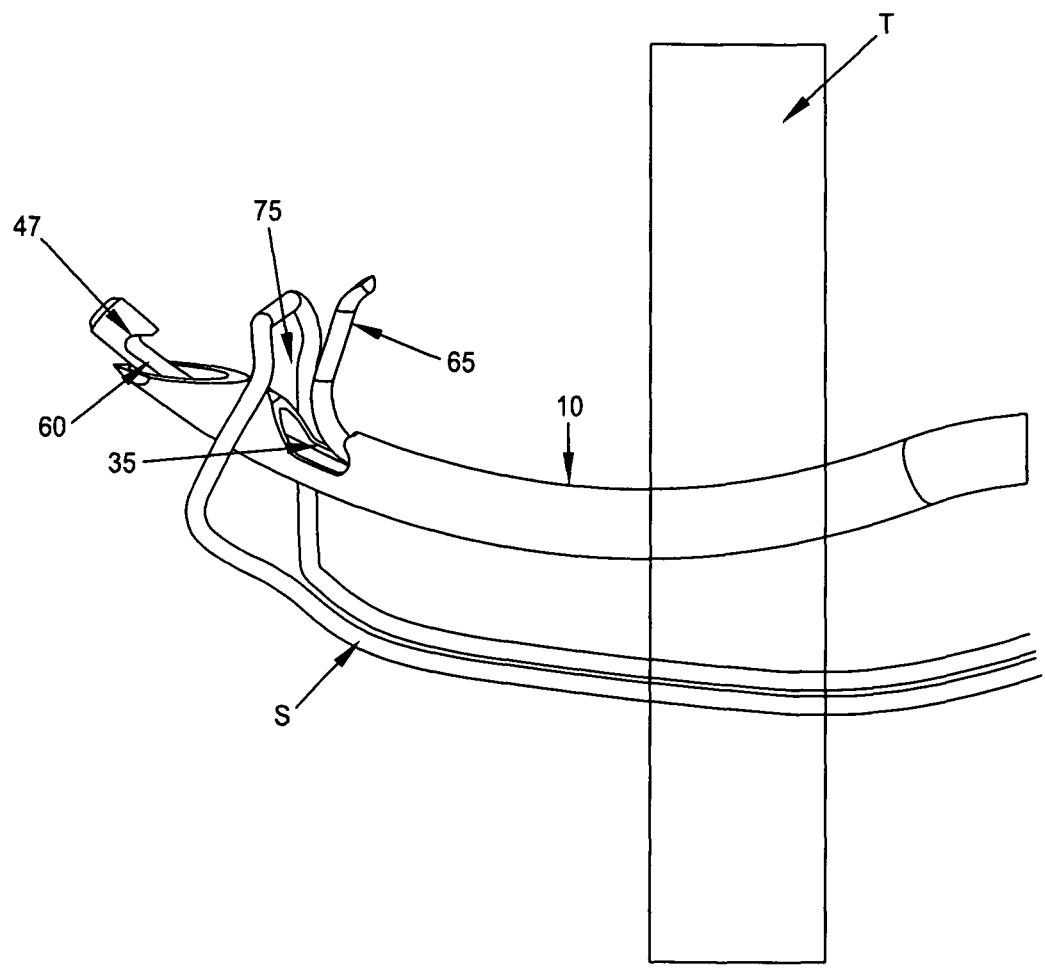
Figure 21:
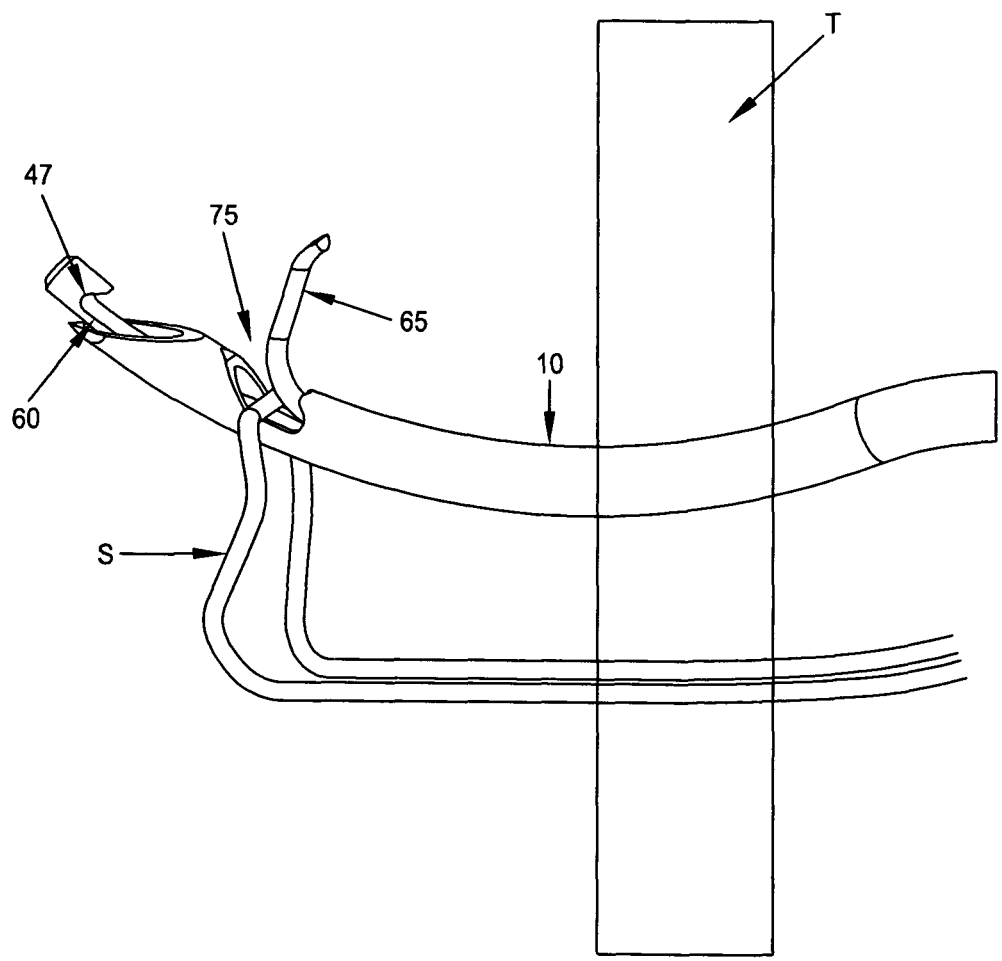

More particularly, in this form of the invention, the suture S is loaded into suture passer 5 on the far side of the tissue T. This is done by first passing suture passer 5 through tissue T so that window 35 resides on the far side of the tissue, and then moving clamping rod 15 distally so that second arm 65 extends out of window 35, substantially perpendicularly to hollow tube 10, whereby to create the aforementioned funnel region 75 (FIGS. 19 and 20). This funnel effect is then used to guide free suture (disposed on the far side of tissue T) into window 35 (see FIG. 21), either by moving suture S relative to suture passer 5 or by moving suture passer 5 relative to suture S or by moving both suture S and suture passer 5 relative to one another. If desired, the suture S may be tensioned so as to help draw it into the window 35.

Figure 22:
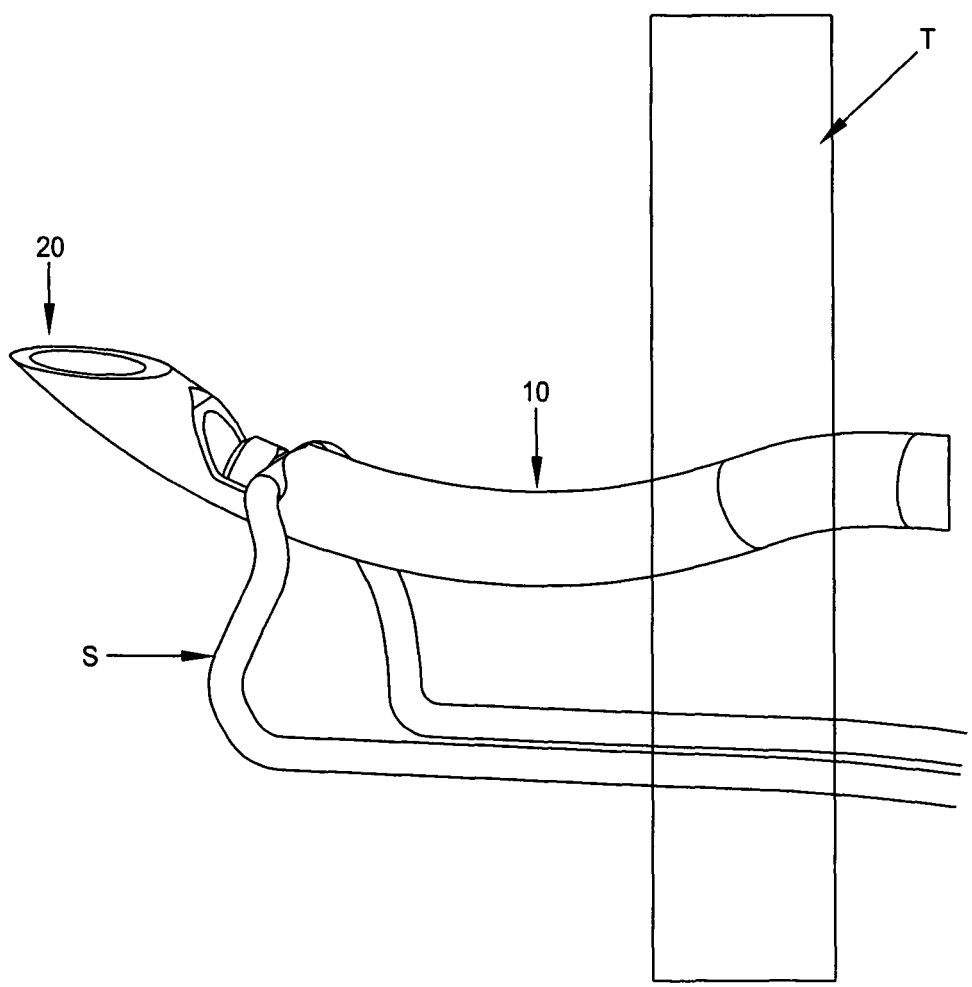
Figure 23:
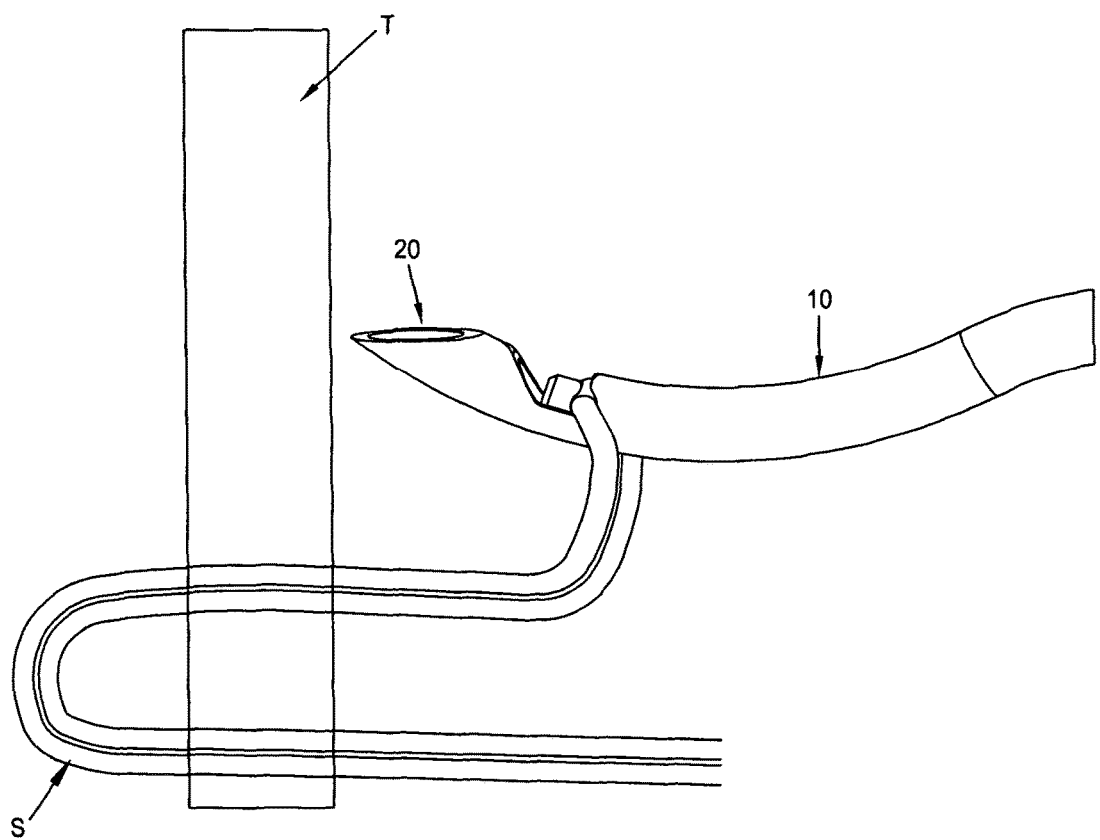
Figure 24:
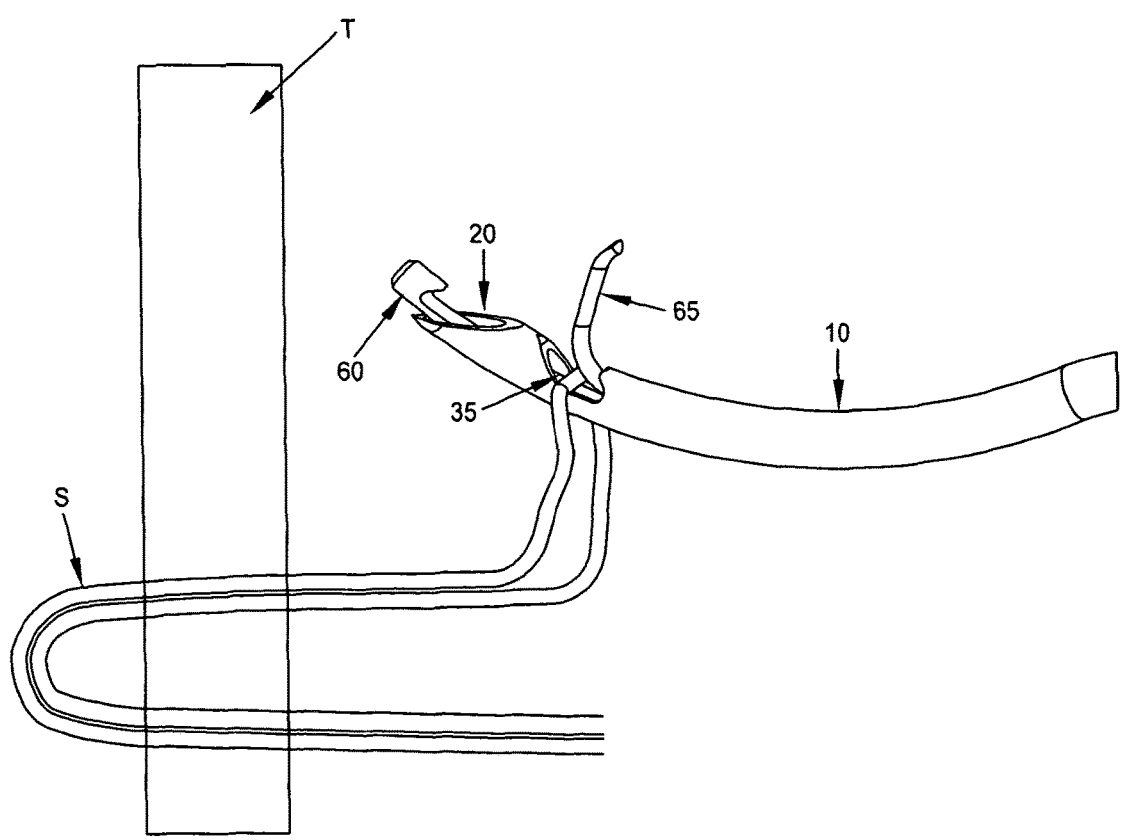

Next, clamping rod 15 is retracted proximally so as to releasably secure suture S between clamping surface 47 and proximal surface 45 of window 35 (FIG. 22). Hollow tube 10 is then retracted proximally through tissue T, carrying suture S therethrough (FIG. 23). If desired, suture S can then be released from suture passer 5 by moving clamping rod 15 distally (FIGS. 24 and 25).

Figure 25:
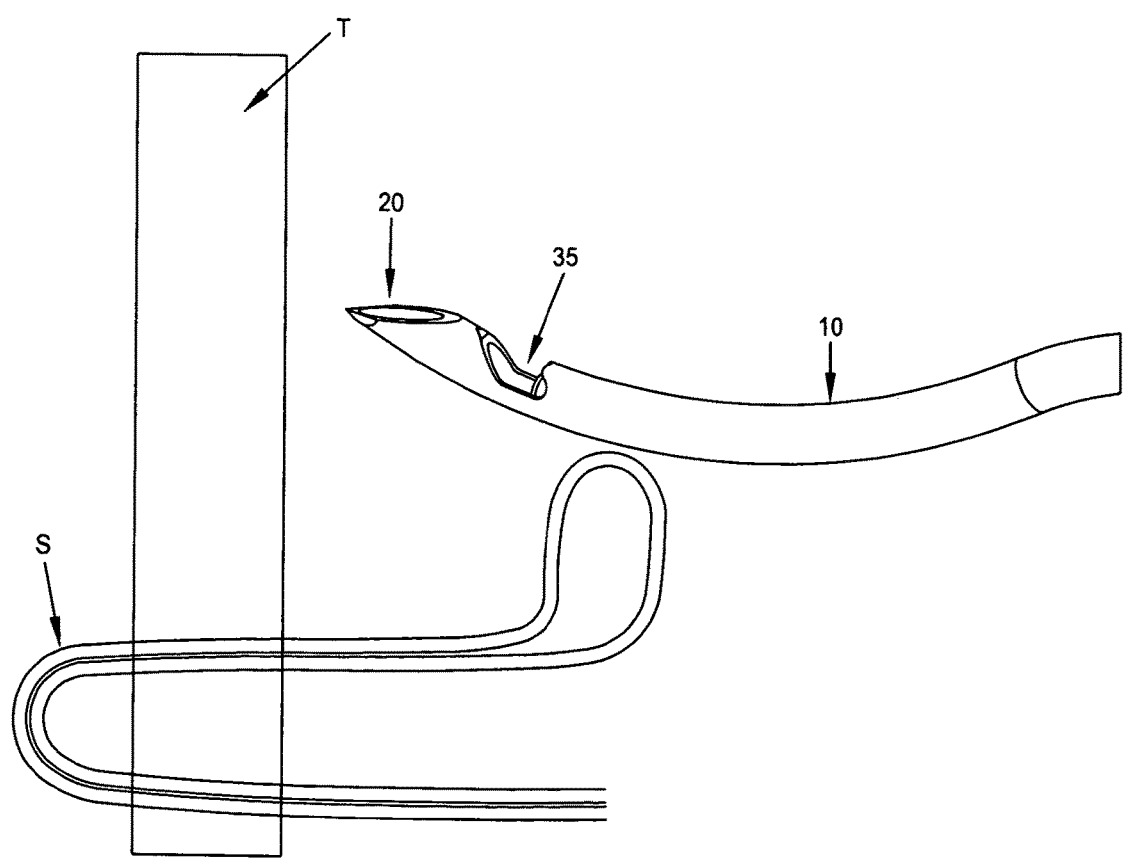

Significantly, by alternating the aforementioned antegrade suture passing procedure (FIGS. 12-18) with the aforementioned retrograde suture passing procedure (FIGS. 19-25), with the needle "plunges" being laterally spaced from one another in the tissue (FIG. 19), a mattress stitch may be placed in the tissue (FIG. 25).

If desired, the novel suture passer 5 may also be used to pass suture S around a side edge of the tissue T, rather than passing the suture S through the tissue. By way of example but not limitation, if the hollow tube 10 is passed around the side edge of the tissue (rather than through it), the suture passer could then be used to retrieve the suture on the far side of the tissue and draw it back around the side edge of the tissue so that the suture is brought to the near side of the tissue.

As described above, the novel suture passer 5 has the ability to both pass (advance) and retrieve (draw) the suture S through and/or around the tissue in a continuous series of steps. This allows the surgeon to complete the desired suture passing without having to remove the suture passer 5 from the portal through which the suture passer 5 is being used. Significantly, this passing/retrieving process can be accomplished with a single instrument, rather than requiring one instrument for passing and a separate instrument for retrieving. This offers significant advantages in convenience and in reducing surgery time.

Alternative Embodiments

Figure 26:
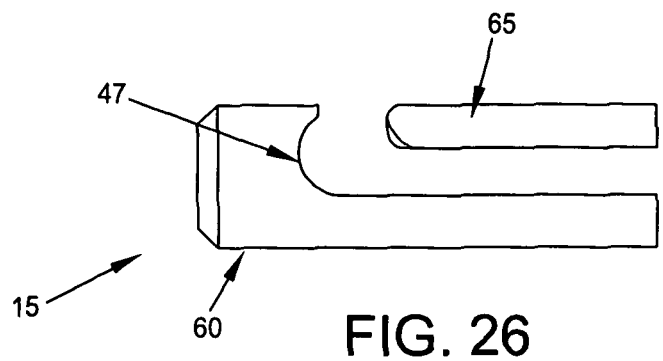
FIGS. 26-29 are schematic views showing various configurations for the clamping surface of the first arm of the clamping rod of the suture passer of FIGS. 1-11.
Figure 27:
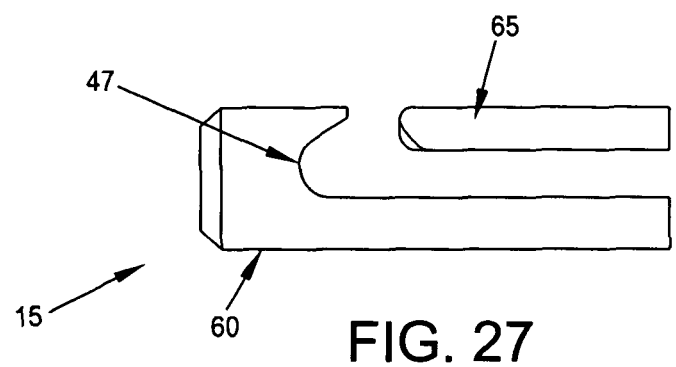
Figure 28:
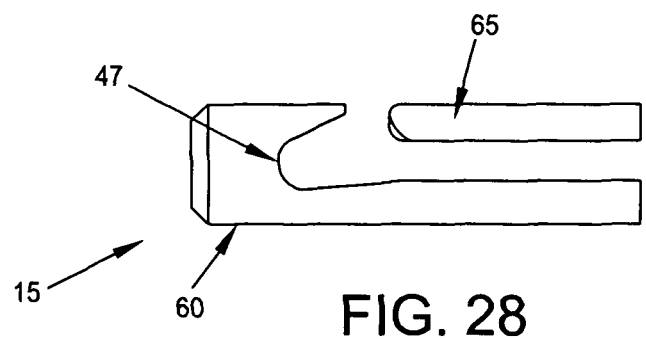
Figure 29:
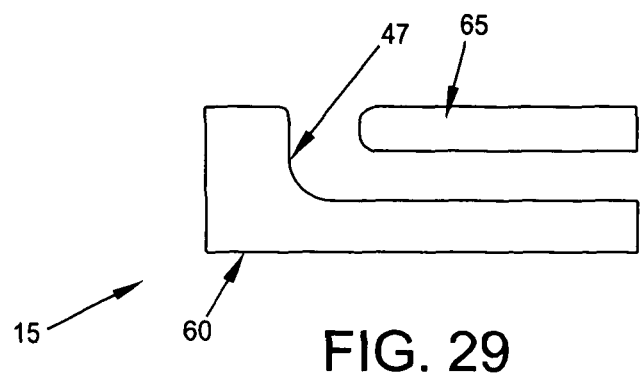

As noted above, clamping surface 47 of clamping rod 15 may take the form of a hook, as shown in FIGS. 1-11. This hook may have various degrees of depth and return, as seen in FIGS. 26-28. Alternatively, clamping surface 47 may be substantially flat, as shown in FIG. 29.

Figure 30:
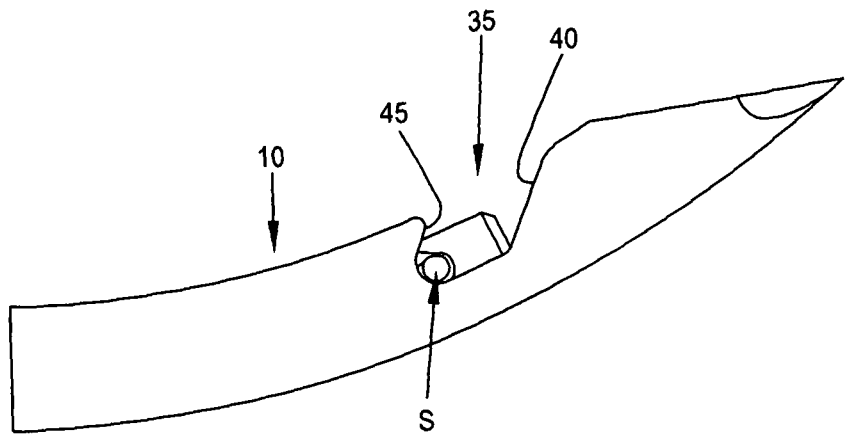
FIGS. 30 and 31 are schematic views showing another configuration for the suture passer of the present invention, wherein the clamping rod and hollow tube are configured so as to allow suture to slide between the clamping rod and the hollow tube.
Figure 31:
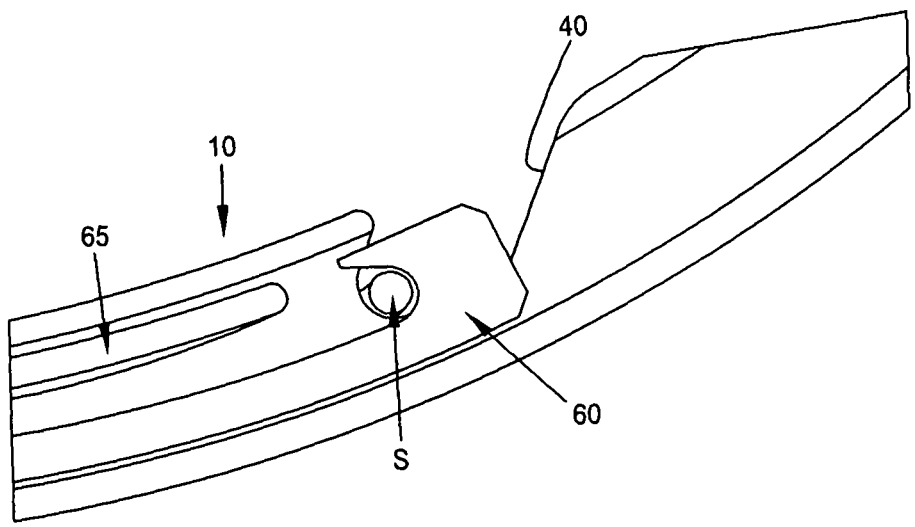

Furthermore, if desired, the suture passer may be constructed so that the suture S is slidably captured—but not clamped—between clamping surface 47 of clamping rod 15 and inclined proximal surface 45 of window 35. In this form of the invention, suture S is slidably captured between the two surfaces (i.e., clamping surface 47 and proximal surface 45), in the manner shown in FIGS. 30 and 31. In this form of the invention, clamping rod 15 may be limited in its proximal travel (e.g., by means of interaction between actuator 72 and handle 23) in order to provide a gap sufficient to slidingly capture, but not bind, suture S. This gap may be equal to, or larger than, the diameter of suture S.

Figure 32:
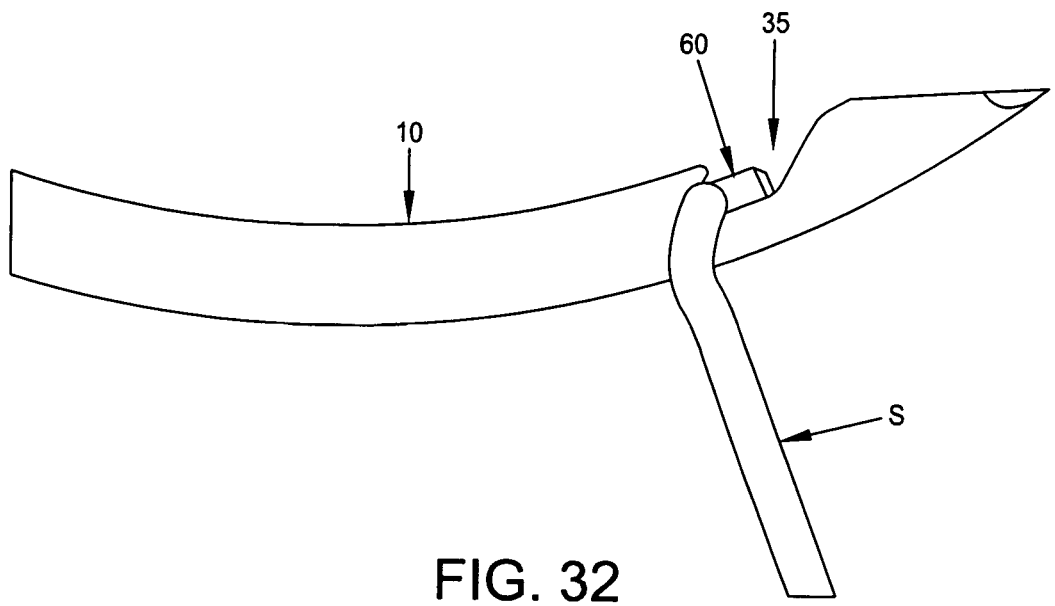
FIGS. 32 and 33 are schematic views showing another configuration for the suture passer of the present invention, wherein the clamping rod is configured to pierce the suture when the clamping rod is moved proximally.
Figure 33:
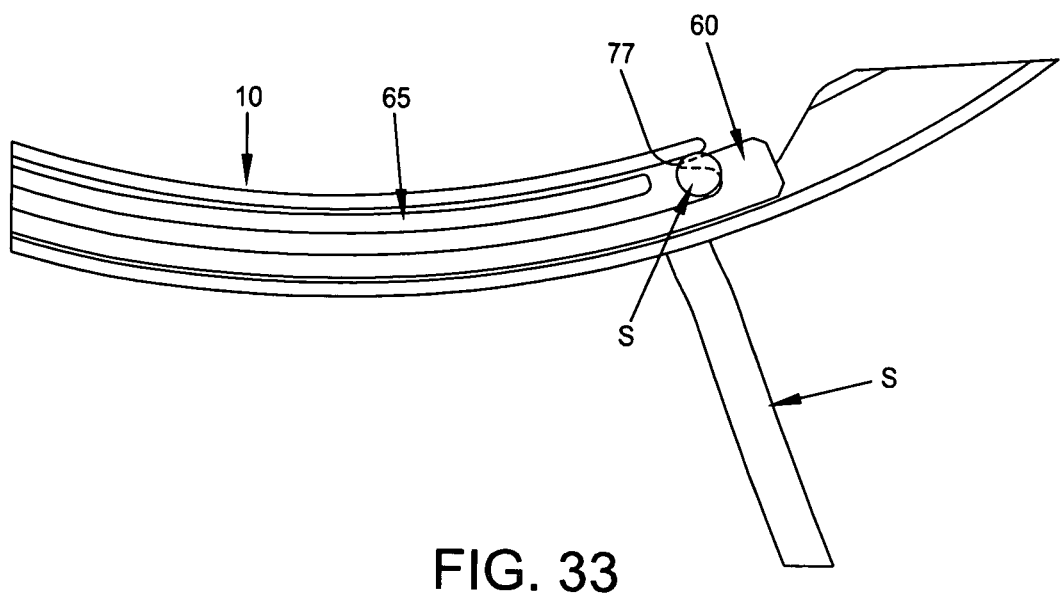

Alternatively, if desired, the clamping rod can be configured to pierce the suture when the clamping rod is moved proximally, as shown in FIGS. 32 and 33. This spearing of the suture can enhance clamping of the suture S to the suture passer 5. By way of example but not limitation, first arm 60 of clamping rod 15 may include a pointed return 77, with pointed return 77 being configured and located such that it will spear suture S when clamping rod 15 is moved proximally.

Figure 34:
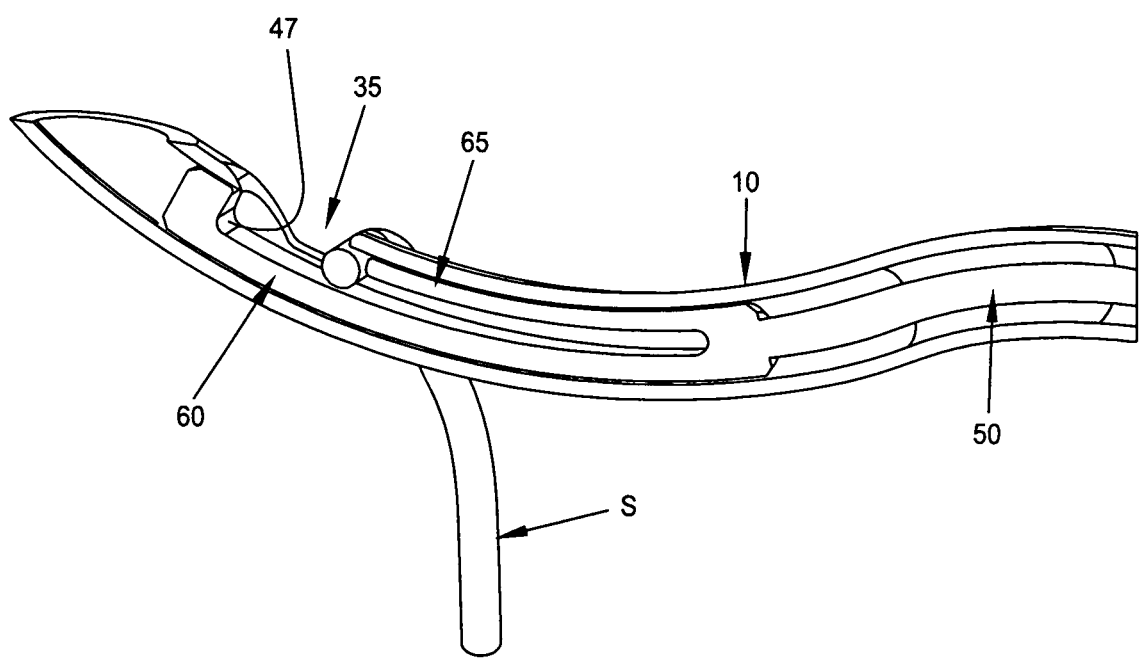
FIGS. 34 and 35 are schematic views illustrating how the lengths of the first and second arms of the bifurcated distal end of the clamping rod can vary from the construction shown in FIGS. 1-11.
Figure 35:
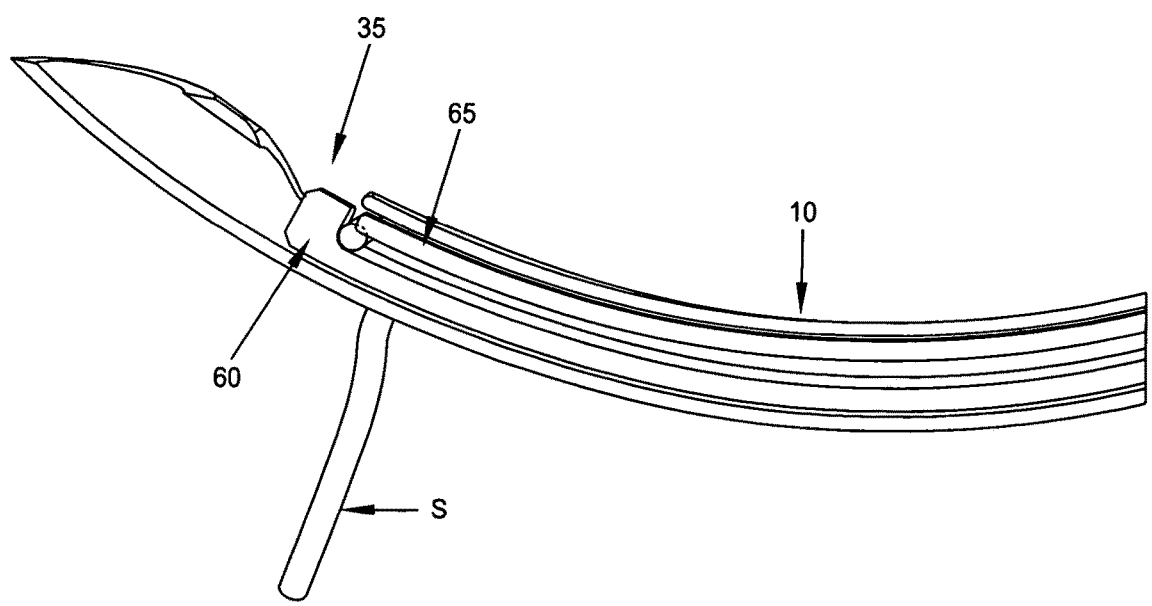

It should be appreciated that the lengths of the first and second arms 60, 65 of clamping rod 15 can vary from the construction shown in FIGS. 1-11. By way of example but not limitation, in one preferred form of the invention, the distance between the distal tip of second arm 65 and clamping surface 47 is approximately the length of window 35, as shown in FIG. 34. In another preferred form of the invention, only a nominal gap is provided between the distal tip of second arm 65 and clamping surface 47 (FIG. 35). This construction can provide for improved capturing of suture S to suture passer 5.

In another form of the present invention, suction may be applied to lumen 30 of hollow tube 10 proximal to window 35. This suction will draw fluid into window 35, and the fluid entering window 35 will assist suture S in seating itself into window 35 as the suture S approaches window 35.

In another form of the present invention, fluid is delivered down lumen 30 of hollow tube 10 so as to assist ejection of suture S from window 35 once the clamping rod 15 has released suture S.

In yet another form of the present invention, hollow tube 10 comprises a second window 35 opposite first window 35, and the distal end of clamping rod 15 is trifurcated so as to form a first arm 60 carrying a pair of clamping surfaces 47 and a pair of second arms 65, with each of the second arms 65 being outboard of first arm 60 and being biased out a window 35. Thus, with this construction, suture can be clamped on either side of hollow tube 10.

In another form of the present invention, the suture passer may further comprise a push rod to assist in ejecting suture S from window 35. The push rod may be a component separate from clamping rod 15 (but slidably movable relative thereto), or it may be integrated with clamping rod 15 (e.g., slidably movable thereon).

Figure 35A:
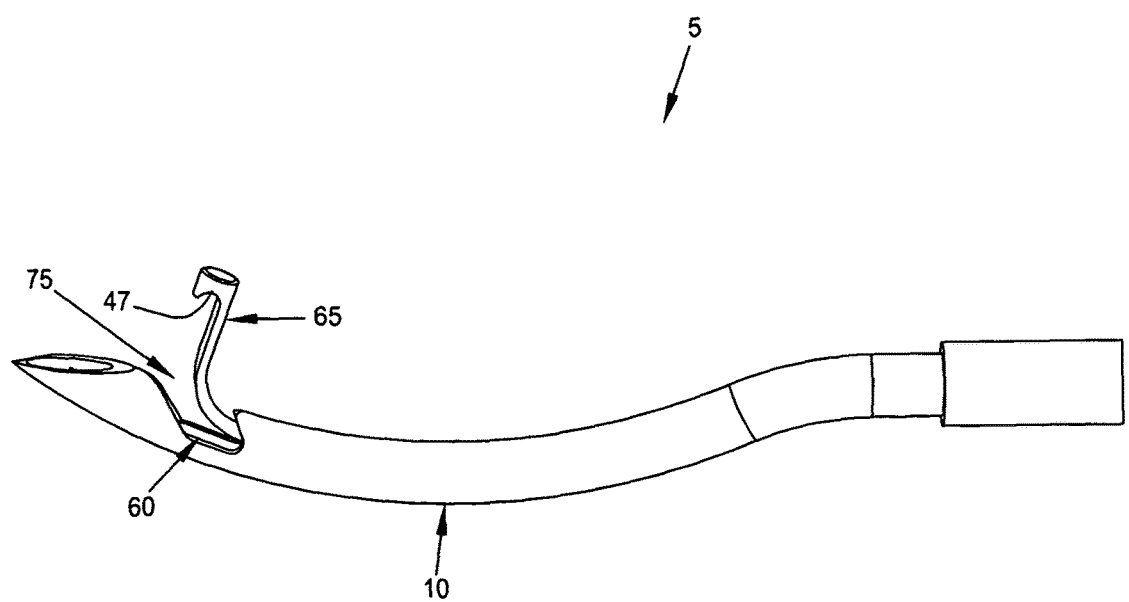
FIGS. 35A-35C are schematic views showing another novel form of suture passer formed in accordance with the present invention.
Figure 35B:
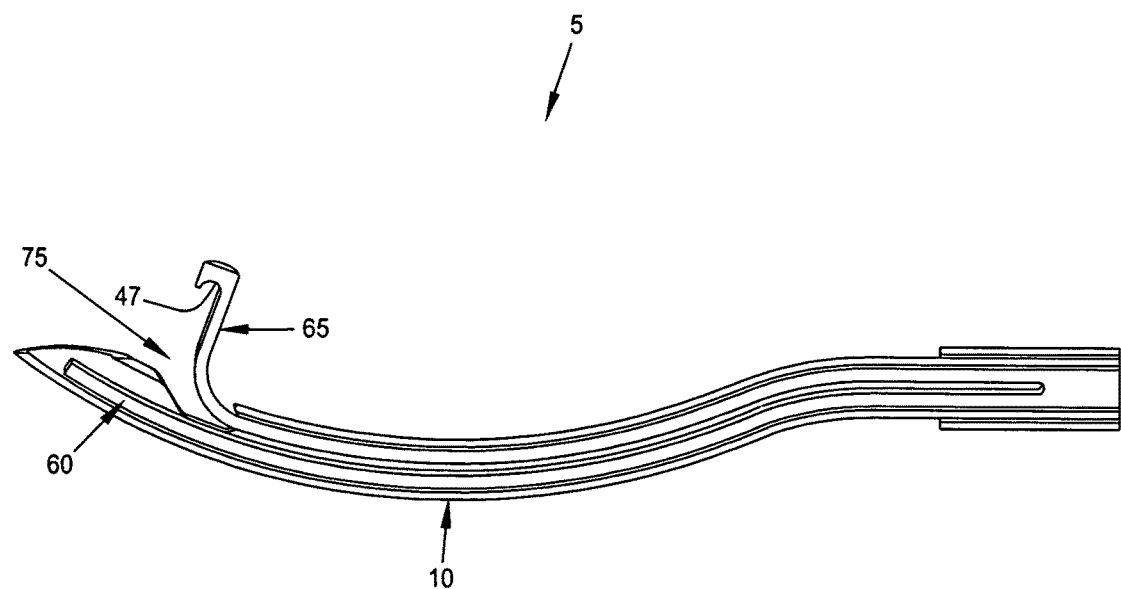
Figure 35C:
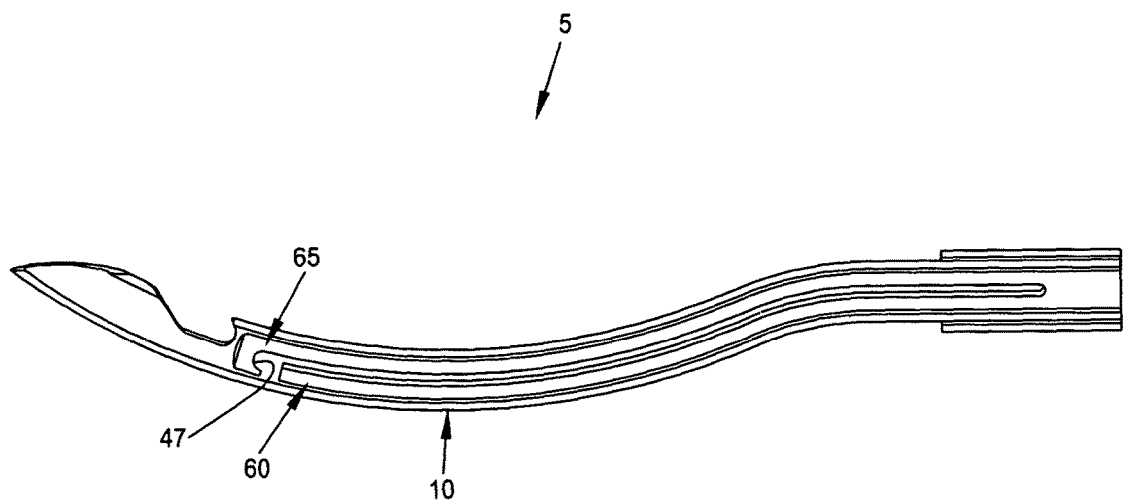
Figure 35D:
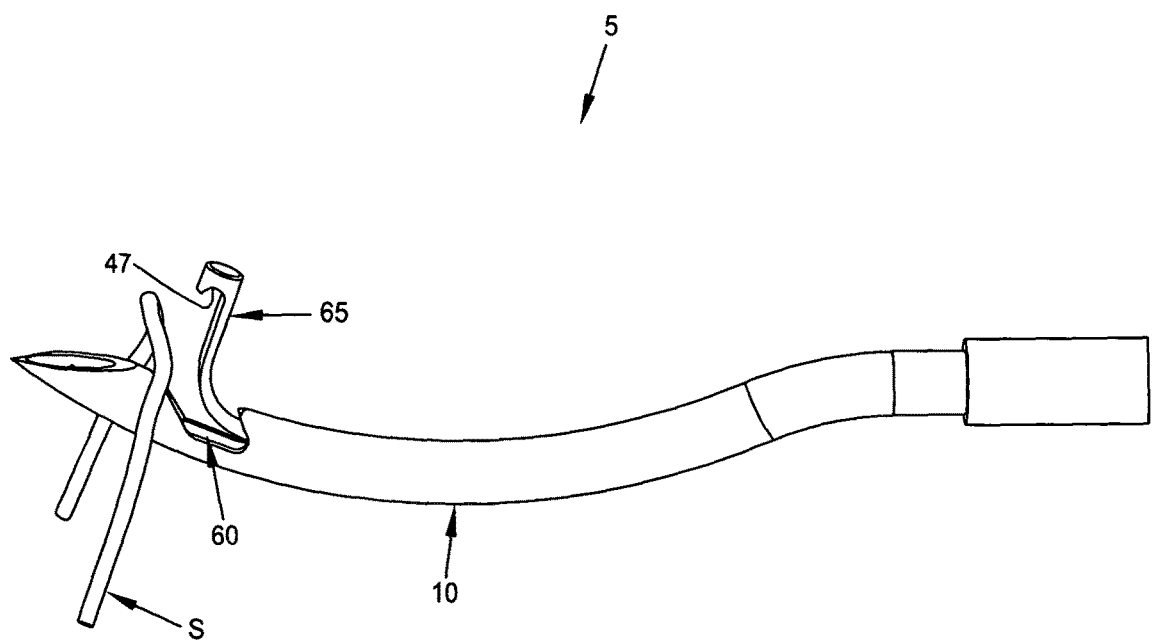
FIGS. 35D-35F are schematic views showing the novel suture passer of FIGS. 35A-35C securing a suture to the distal end of the suture passer.
Figure 35E:
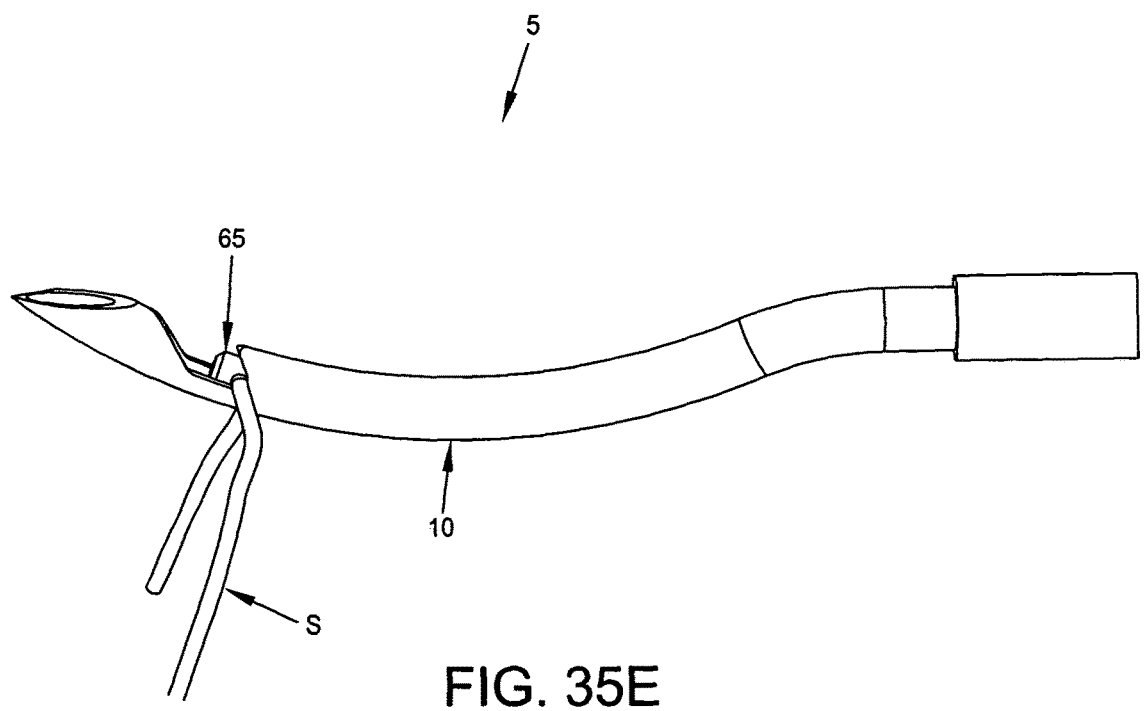
Figure 35F:
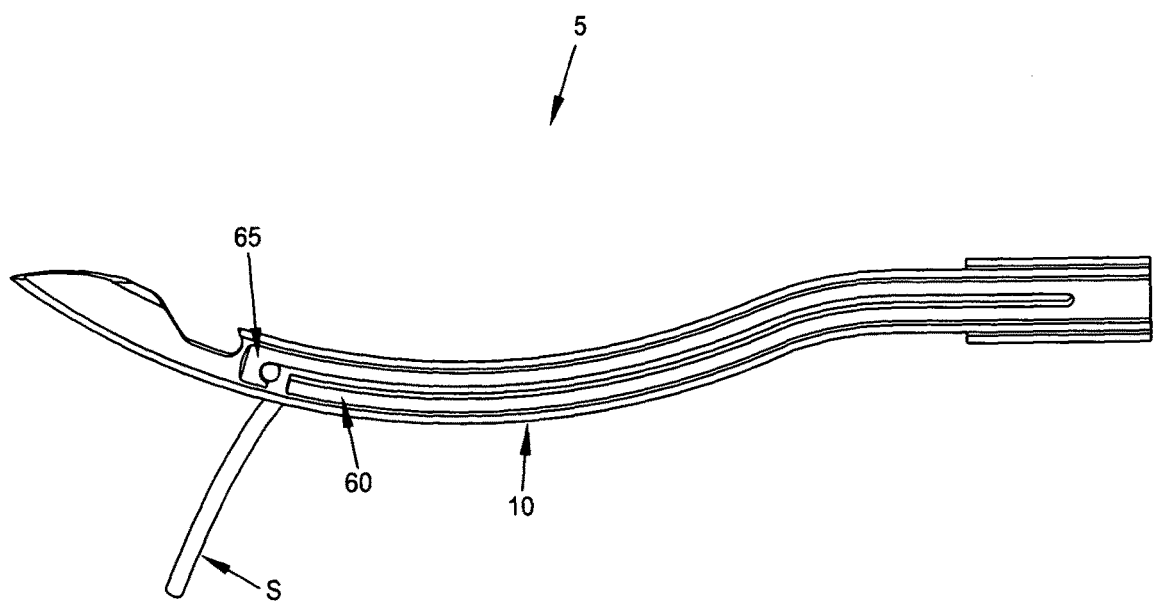

Looking next at FIGS. 35A-35C, it is also possible to form novel suture passer 5 so that (i) first arm 60 is shorter than second arm 65, and (ii) clamping surface 47 is formed on the outwardly biased second arm 65 (rather than on first arm 60). In this form of the invention, funnel region 75 is formed between the distal end of shaft 10 and first arm 60. FIGS. 35D-35F show the novel suture passer of FIGS. 35A-35C securing a suture S to the distal end of the suture passer.

Furthermore, if desired, where clamping surface 47 is formed on the outwardly biased second arm 65 (e.g., in the manner shown in FIGS. 35A-35C and FIGS. 35D-35F), first arm 60 may be omitted entirely, in which case the distal end of clamping rod 15 preferably comprises only outwardly biased second arm 65.

Figure 35G:
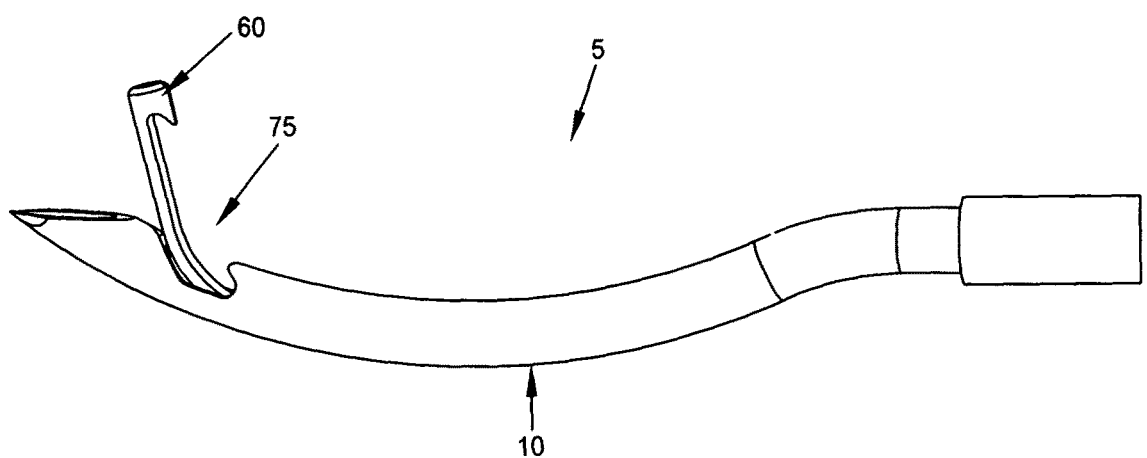
FIGS. 35G-35I are schematic views showing another novel form of suture passer formed in accordance with the present invention.
Figure 35H:
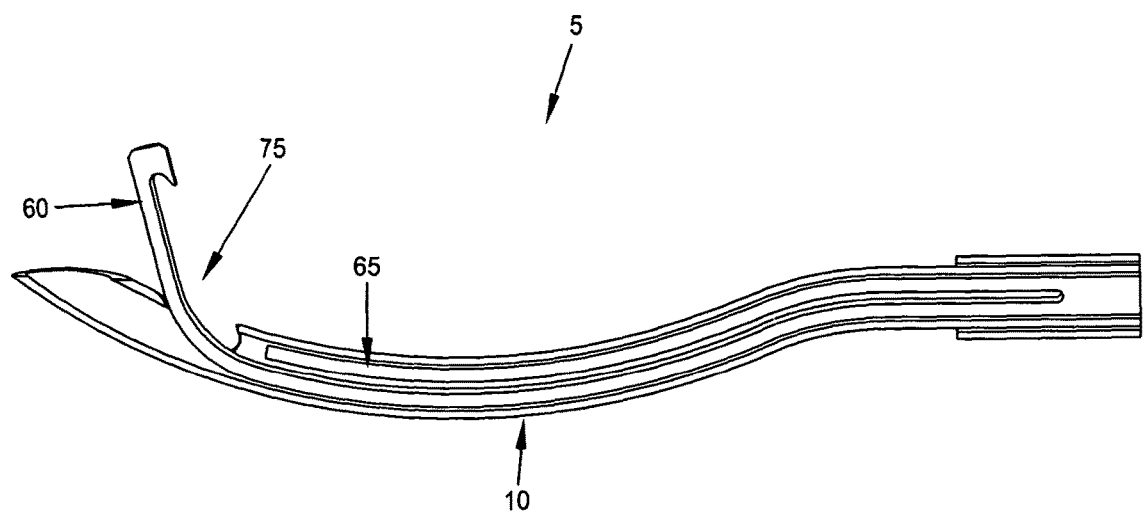
Figure 35I:
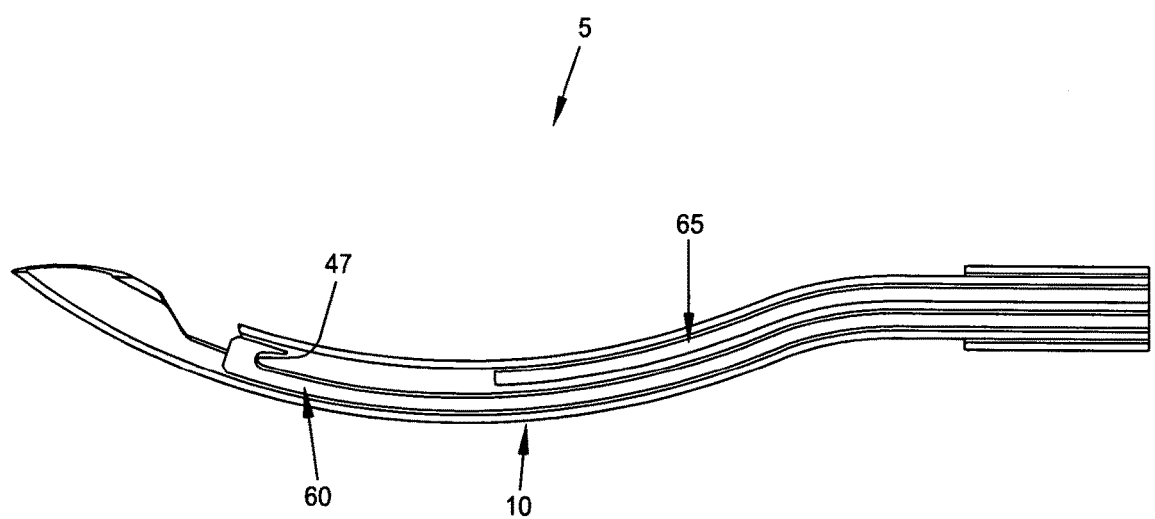
Figure 35J:
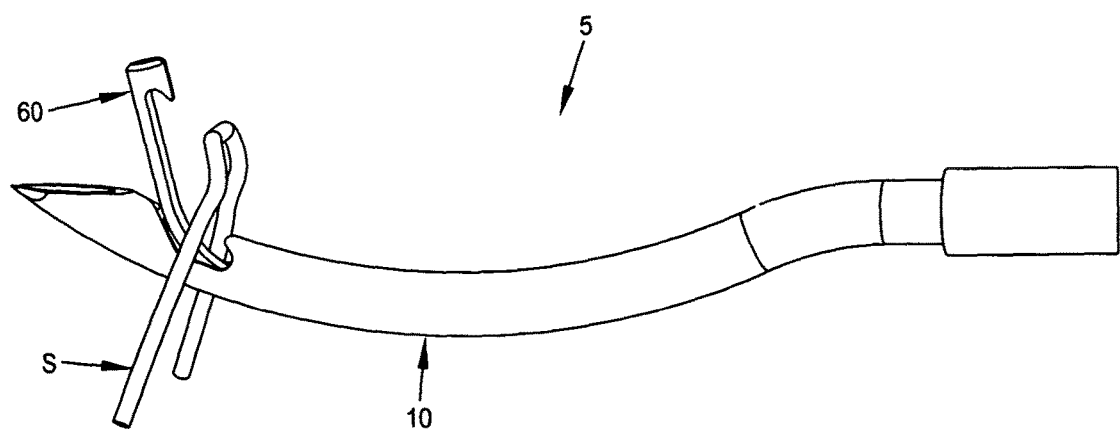
FIGS. 35J-35L are schematic views showing the novel suture passer of FIGS. 35G-35I securing a suture to the distal end of the suture passer.
Figure 35K:
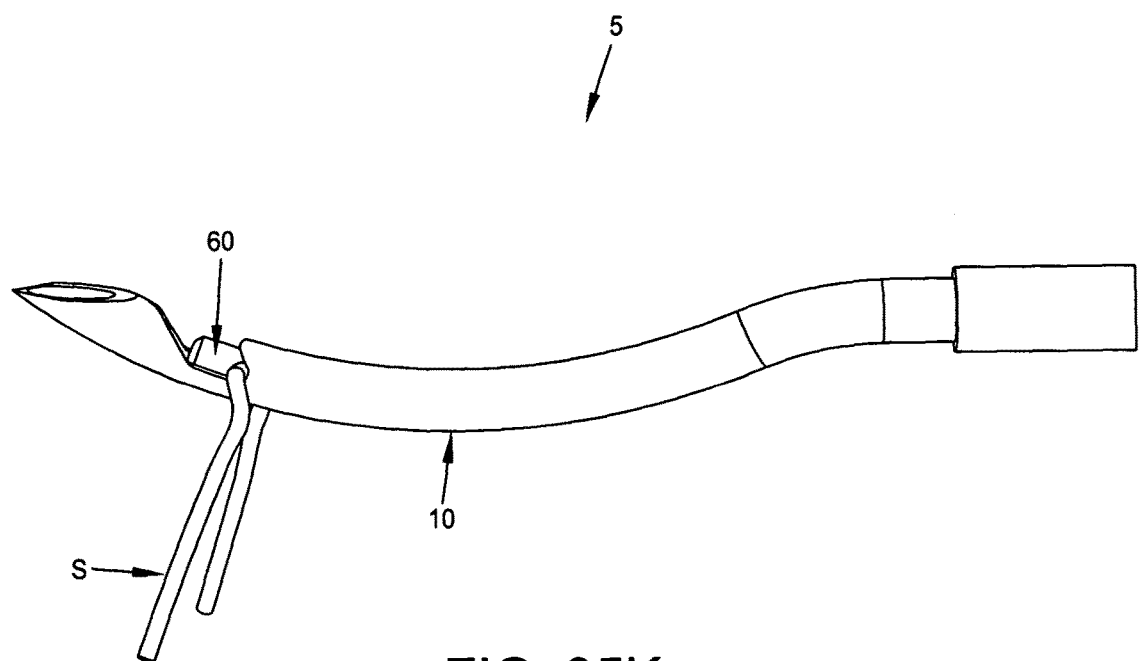
Figure 35L:
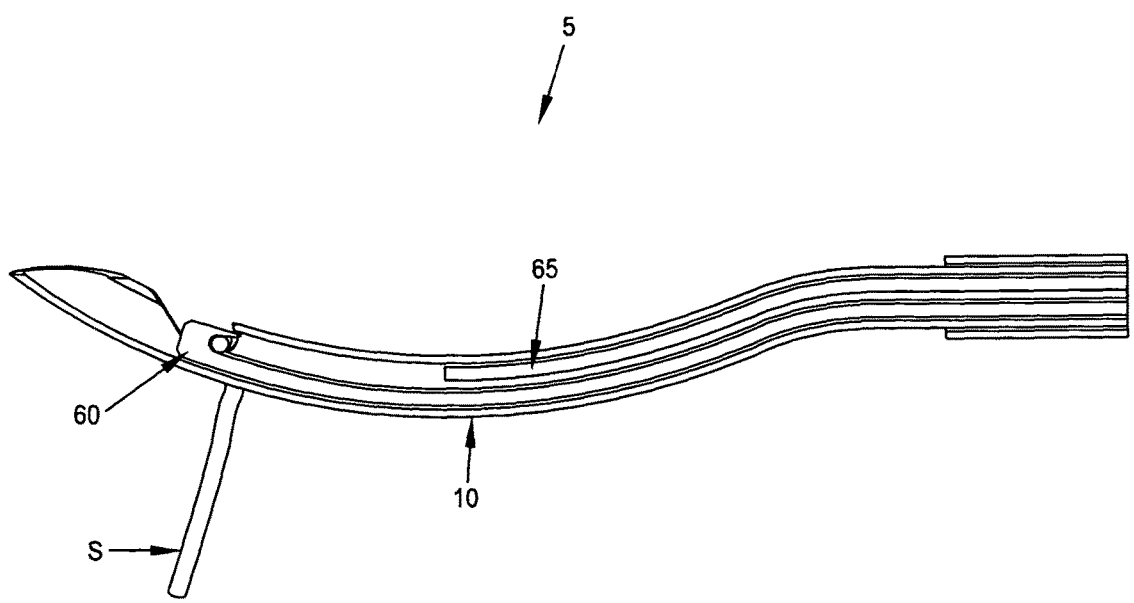

In another form of the present invention, and looking now at FIGS. 35G-35I, novel suture passer 5 may be constructed so that first arm 60 (carrying clamping surface 47) is outwardly biased, so that first arm 60 (and clamping surface 47) extends out window 35 when clamping rod 15 is moved distally. In this form of the invention, the funnel region 75 is formed between the distal end of shaft 10 and first arm 60. FIGS. 35J-35L show the novel suture passer of FIGS. 35G-35I securing a suture S to the distal end of the suture passer.

Furthermore, if desired, where first arm 60 is outwardly biased and carries clamping surface 47 (e.g., in the manner shown in FIGS. 35G-35I and FIGS. 35J-35L), second arm 65 may be omitted entirely, in which case the distal end of clamping rod 15 preferably comprises only outwardly biased first arm 60 (with clamping surface 47).

Figure 35M:
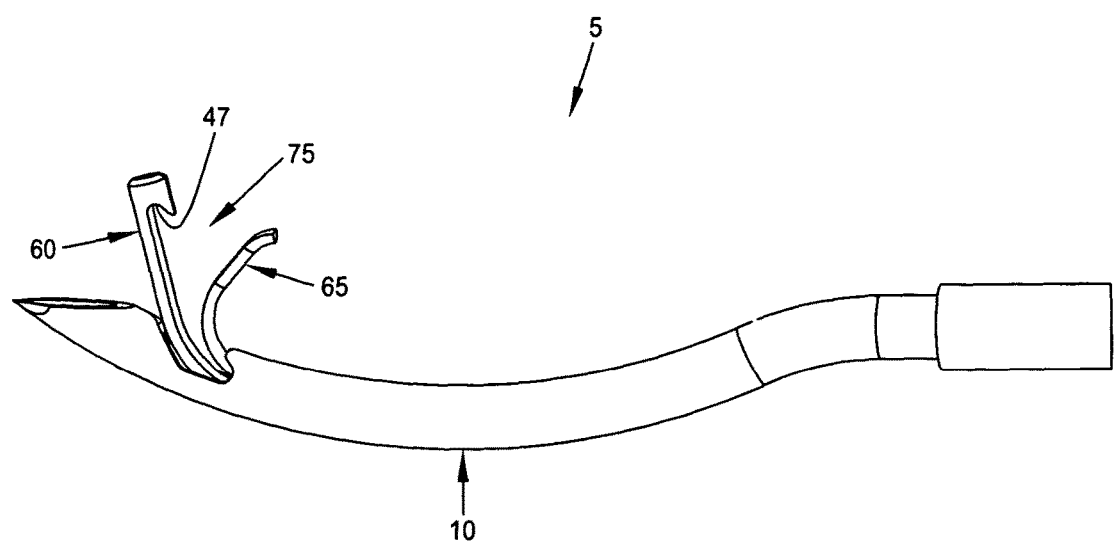
FIGS. 35M-35O are schematic views showing another novel form of suture passer formed in accordance with the present invention.
Figure 35N:
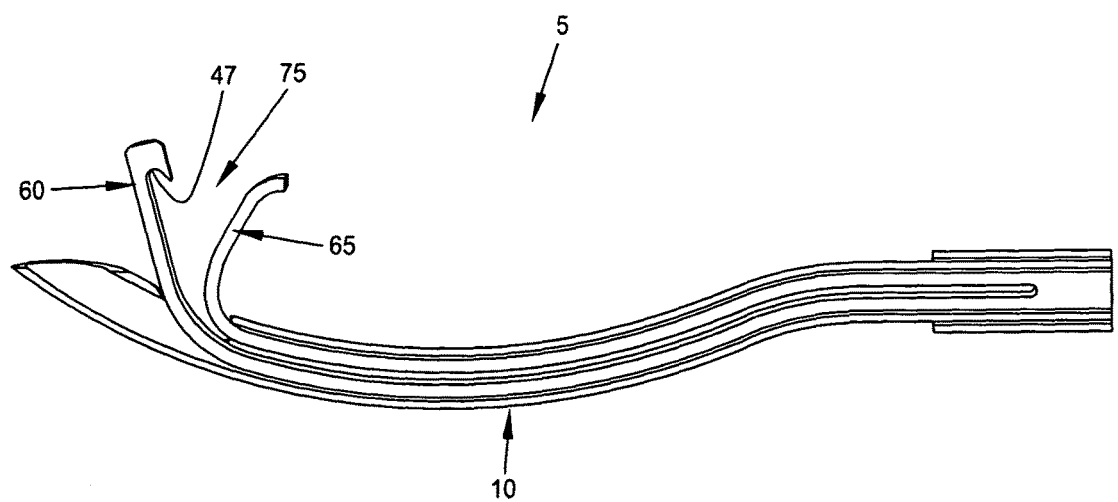
Figure 35O:
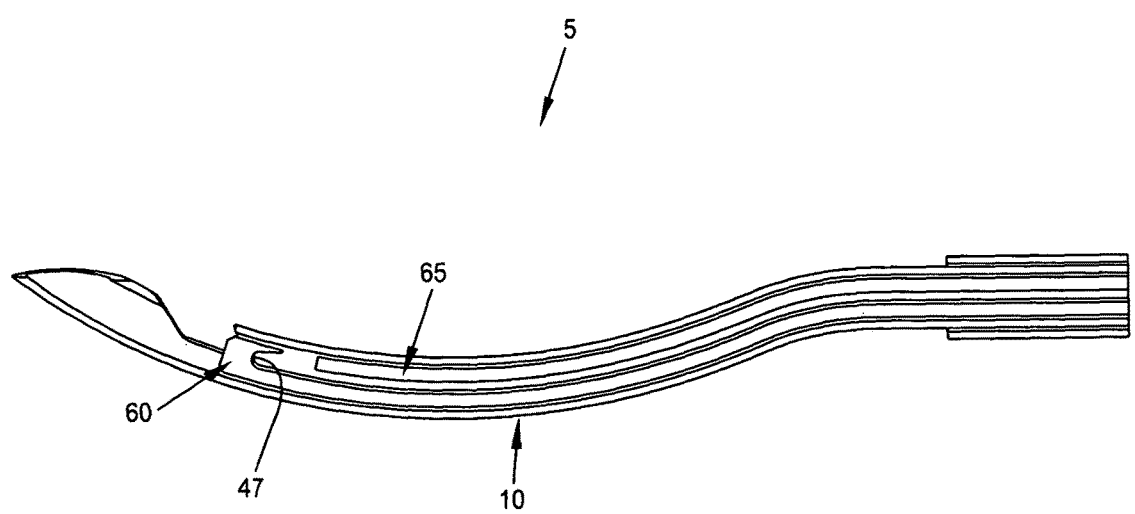
Figure 35P:
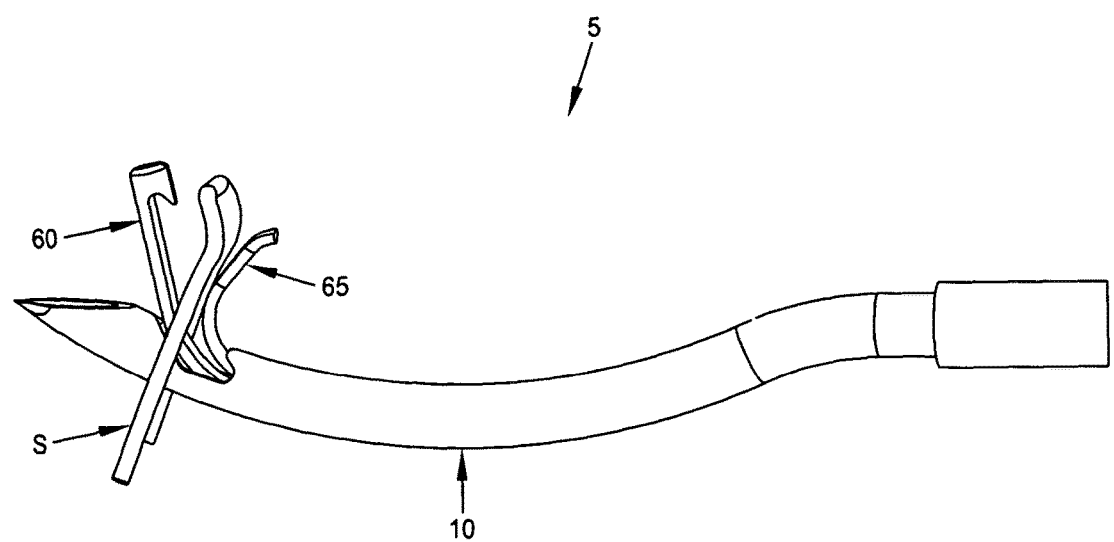
FIGS. 35P-35R are schematic views showing the novel suture passer of FIGS. 35M-35O securing a suture to the distal end of the suture passer.
Figure 35Q:
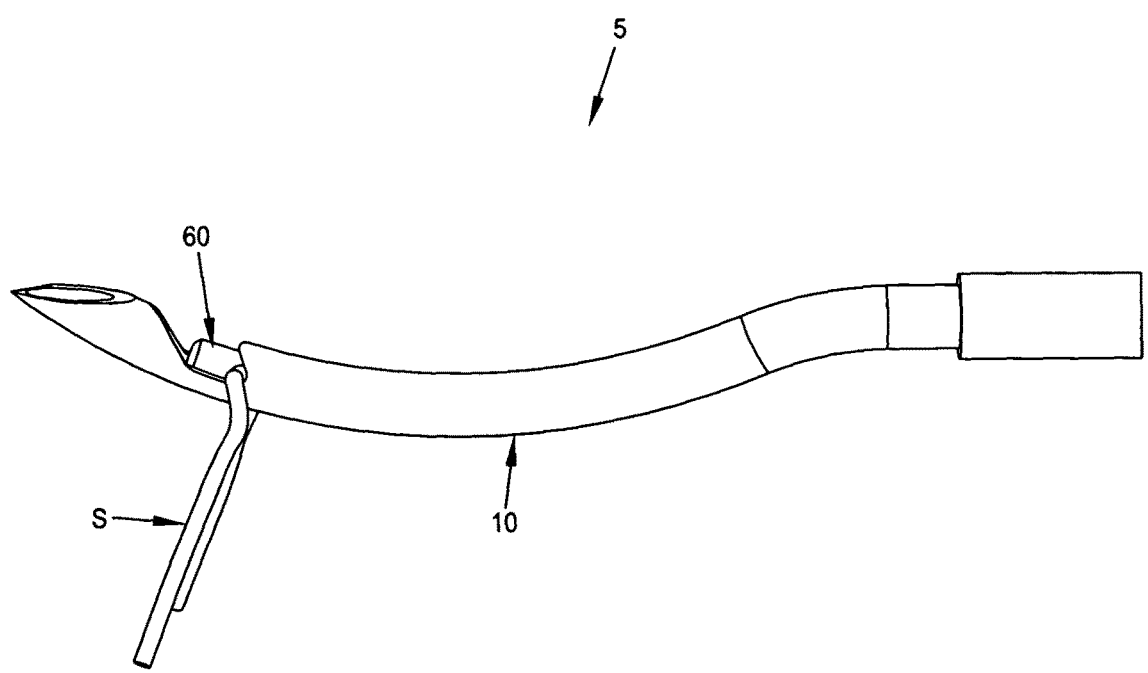
Figure 35R:
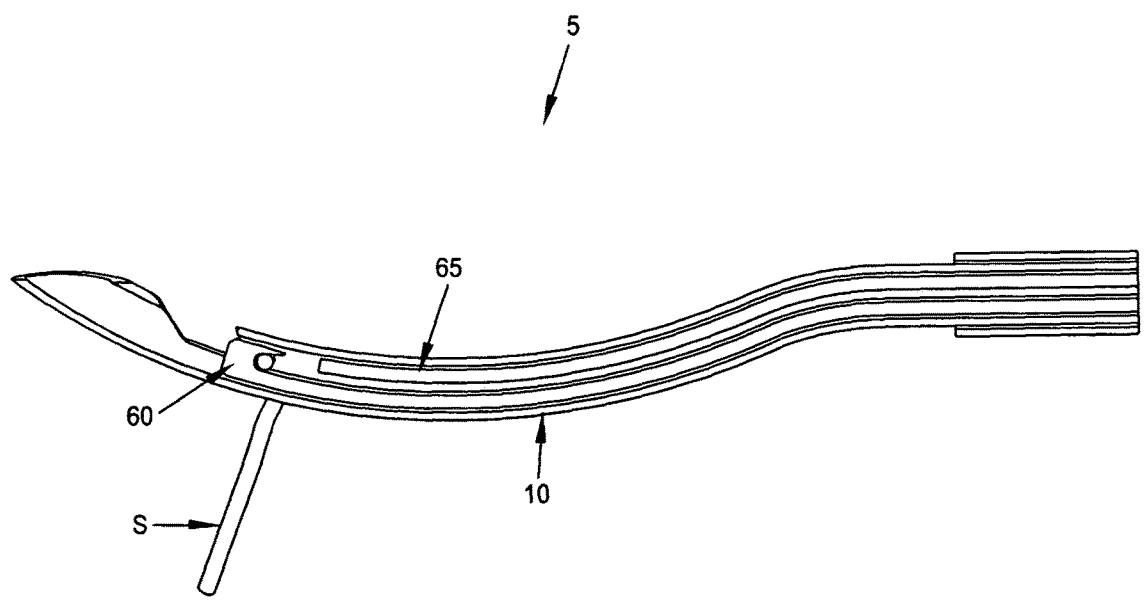
Figure 36:
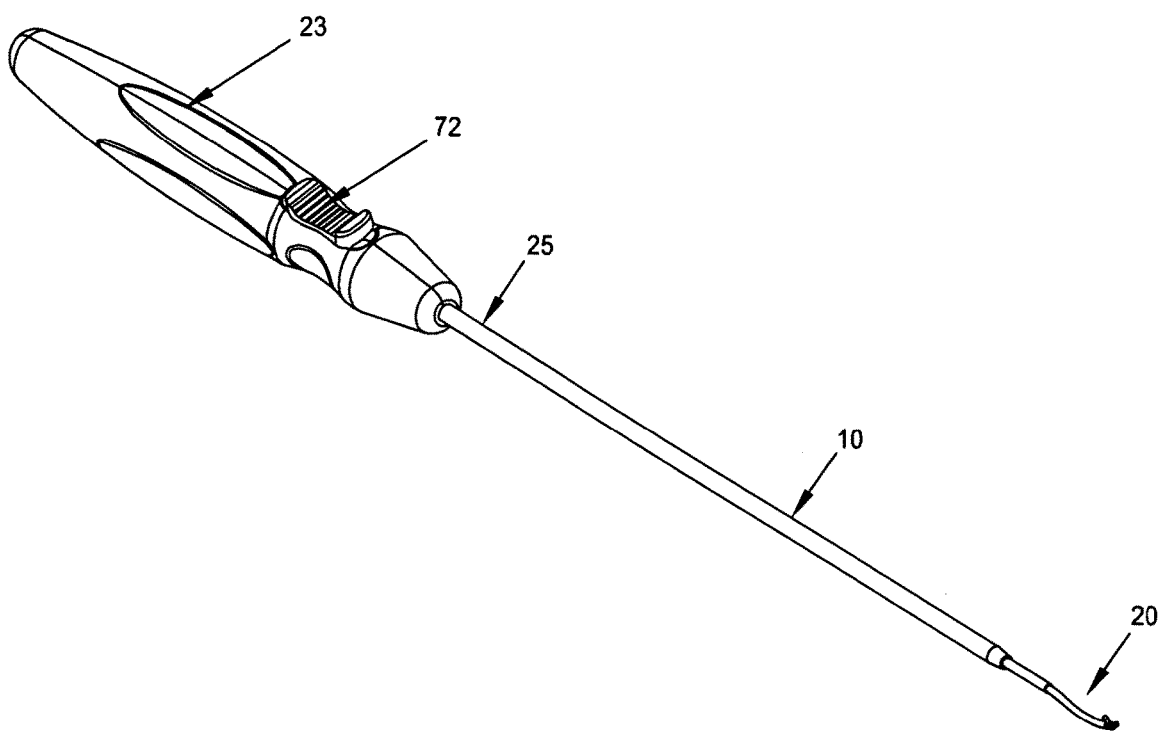
FIGS. 36-40 are schematic views showing another novel form of suture passer formed in accordance with the present invention.
Figure 37:
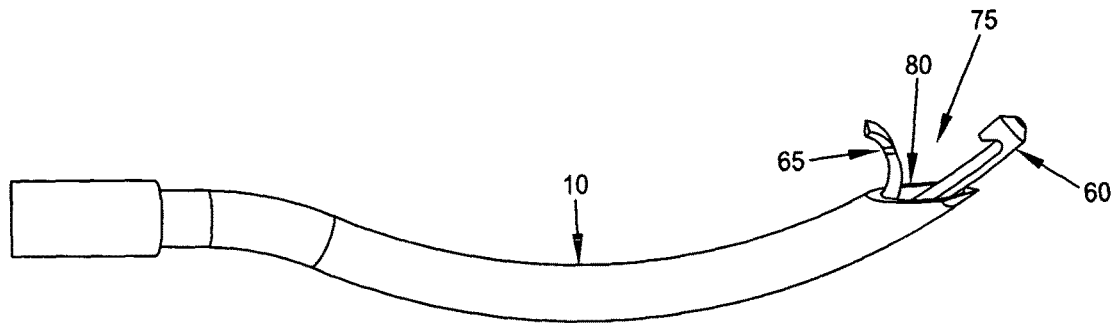
Figure 38:
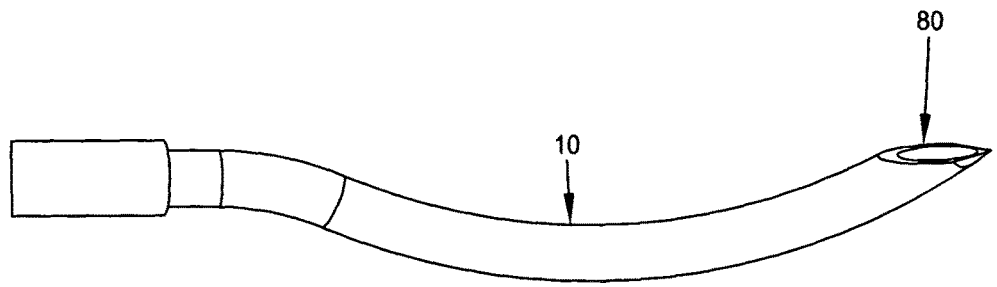
Figure 39:
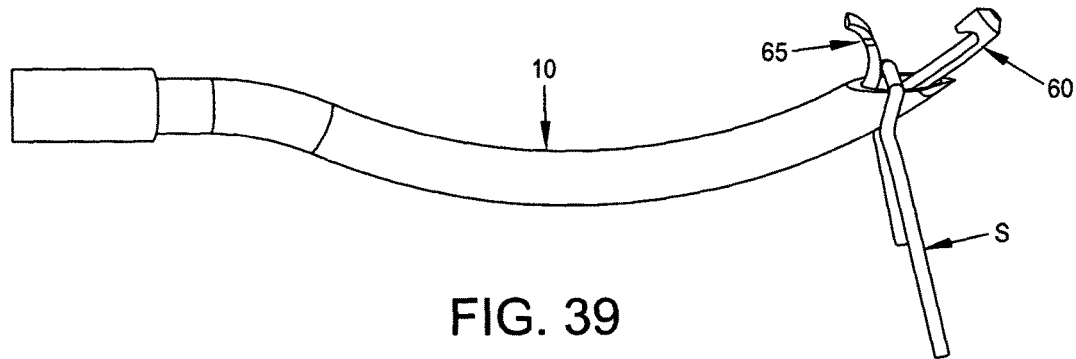
Figure 40:
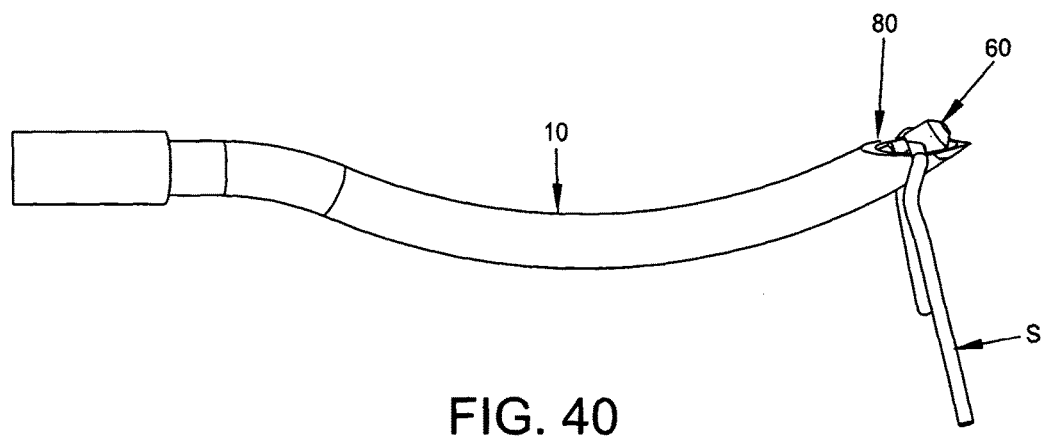
Figure 41:
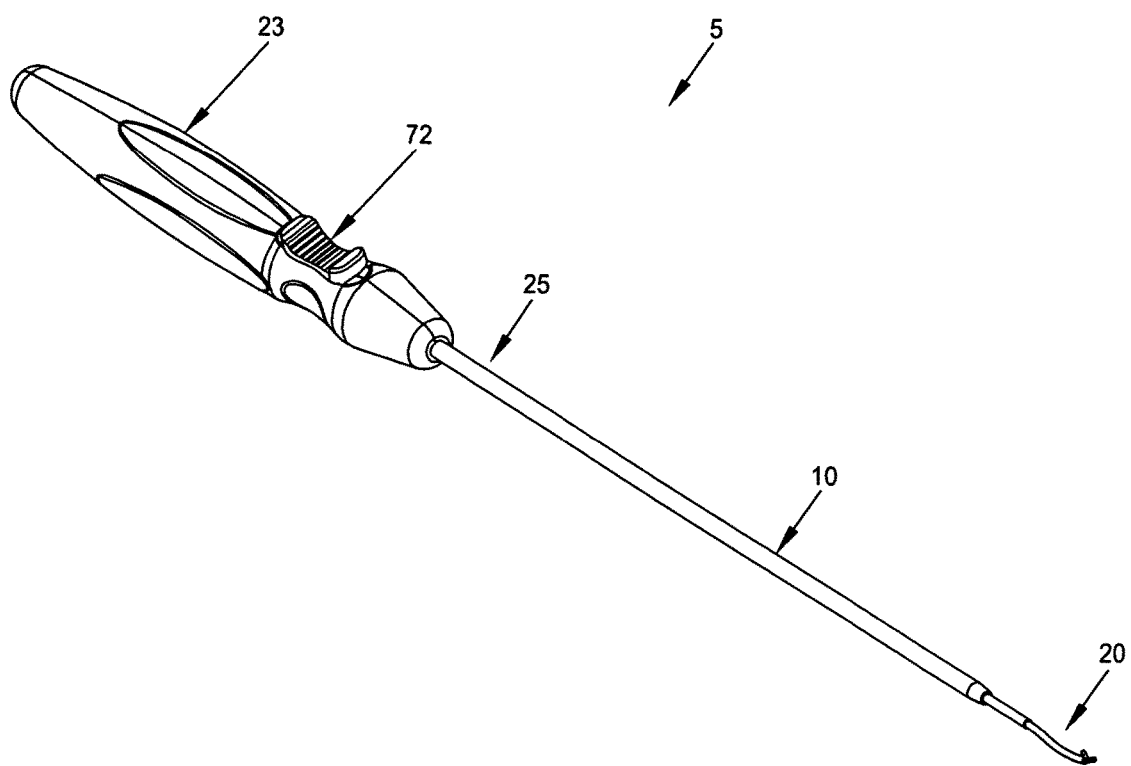
FIGS. 41-47 are schematic views showing still another novel form of suture passer formed in accordance with the present invention.
Figure 42:
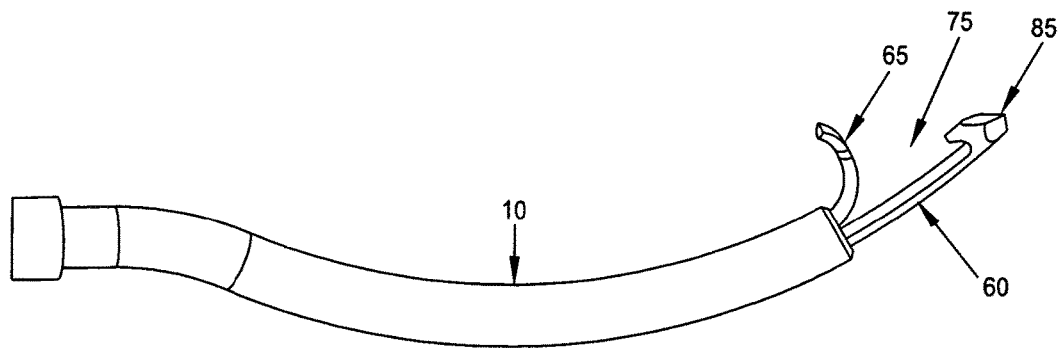
Figure 43:
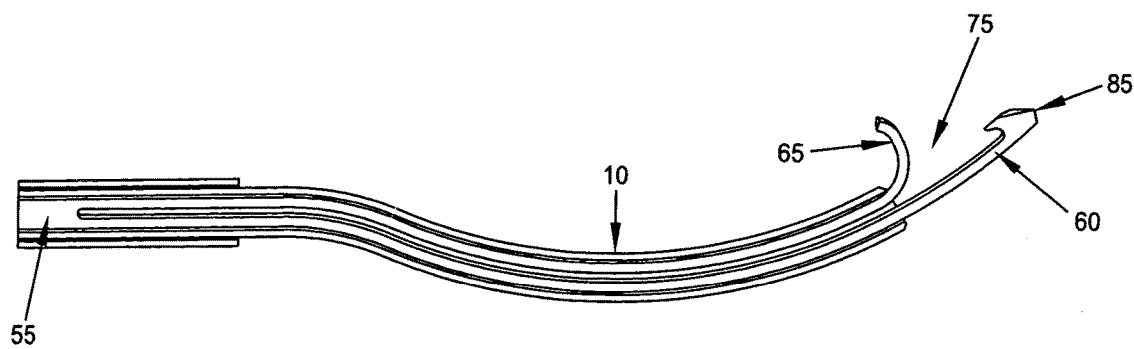
Figure 44:
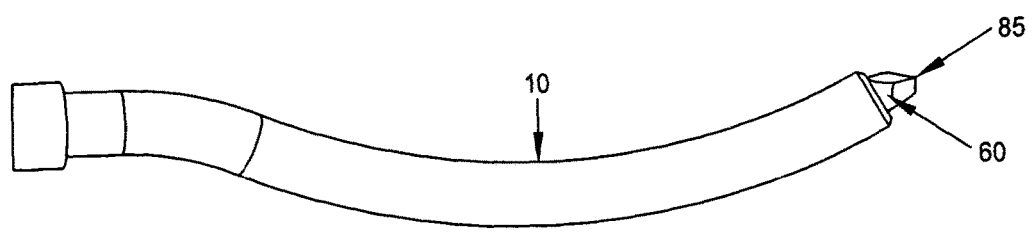
Figure 45:
Figure 46:
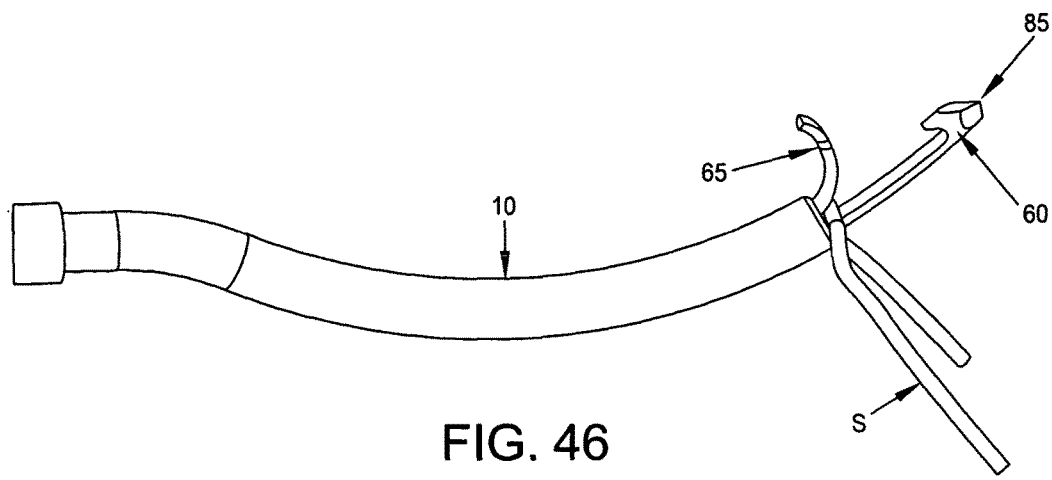
Figure 47:
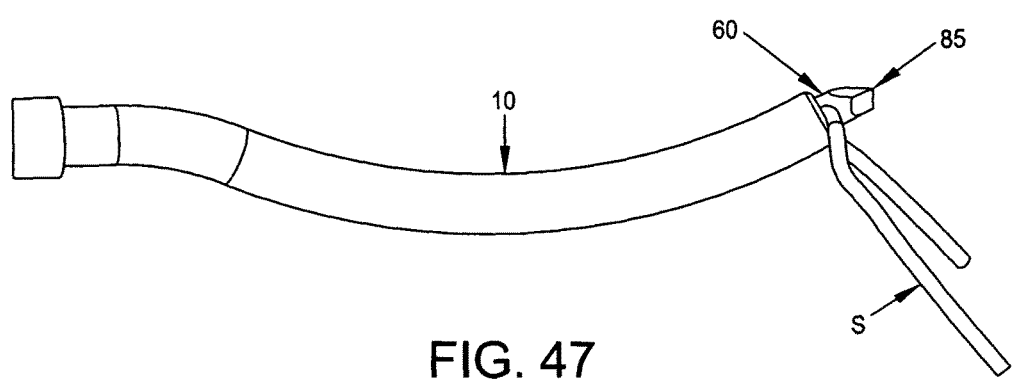
Figure 48:
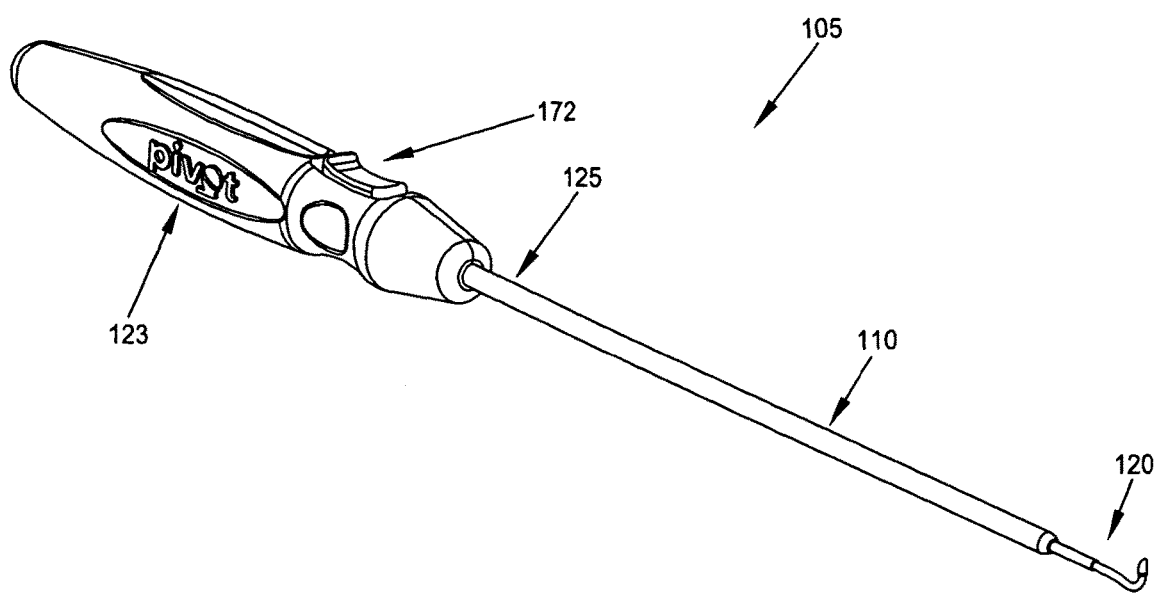
FIGS. 48-60 are schematic views showing yet another novel form of suture passer formed in accordance with the present invention.
Figure 49:
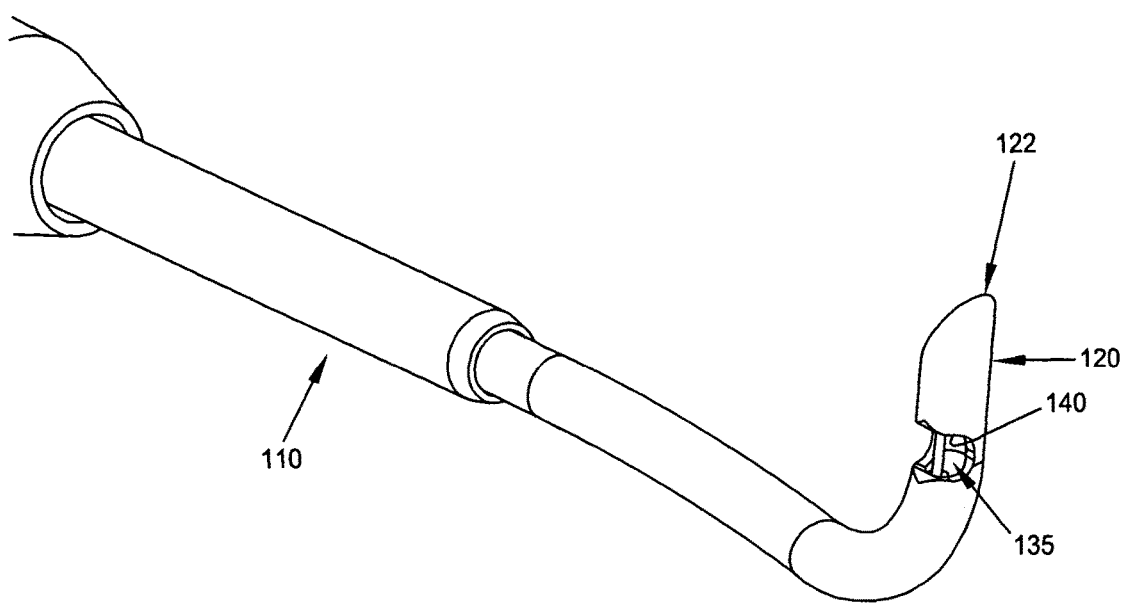

In still another form of the present invention, and looking now at FIGS. 35M-35O, novel suture passer 5 may be constructed so that both first arm 60 (carrying clamping surface 47) and second arm 65 are outwardly biased, so that both first arm 60 (and clamping surface 47) and second arm 65 extend out window 35 when clamping rod 15 is moved distally. In this form of the invention, funnel region 75 is formed between first arm 60 and second arm 65. FIGS. 35P-35R show the novel suture passer of FIGS. 35M-35O securing a suture S to the distal end of the suture passer.

In another form of the present invention, and looking now at FIGS. 36-40, window 35 may be eliminated, and clamping rod 15 may clamp suture S against the distal end surface 80 of hollow tube 10.

Furthermore, if desired, and looking now at FIGS. 41-47, the distal end surface 80 of hollow tube 10 can be disposed substantially perpendicular to the longitudinal axis of hollow tube 10, whereby to enhance clamping of suture S against distal end surface 80 of hollow tube 10. In this construction, it may be desirable to provide a sharp point 85 to the distal end of first arm 60, in order to facilitate passage of the suture passer through tissue.

Handle

As noted above, suture passer 5 preferably comprises a handle 23, and handle 23 preferably comprises an actuator 72 which actuates clamping rod 15 so as to clamp and/or release suture S. If desired, actuator 72 may comprise a lock or detent which maintains the position of clamping rod 15 relative to hollow tube 10. For example, the lock or detent may hold the clamping rod in a distal position and/or in a proximal position (e.g., while it is clamping suture S).

Actuator 72 may also comprise a spring to bias clamping rod 15 proximally or distally. In one preferred form of the invention, this spring biases the clamping rod in a proximal direction (for example, to clamp suture S between clamping surface 47 and inclined surface 45).

Novel "Spear" Suture Passer

Looking next at FIGS. 48-60, there is shown a novel suture passer 105 also formed in accordance with the present invention. Suture passer 105 will sometimes hereinafter be referred to as the "spear" suture passer.

More particularly, the spear suture passer 105 generally comprises an outer shaft tube 110, an inner guide tube 112 fixedly disposed within the interior of outer shaft tube 110, and a suture spear 116 slidably disposed within the lumen of inner guide tube 112, as will hereinafter be discussed in further detail.

More particularly, outer shaft tube 110 comprises a distal end 120 preferably terminating in a sharp point 122, and a proximal end 125 preferably terminating in a handle 123, with a lumen 130 extending therebetween. It will be appreciated that the pointed outer shaft tube 110 essentially comprises a hollow needle adapted to pierce tissue.

Figure 50:
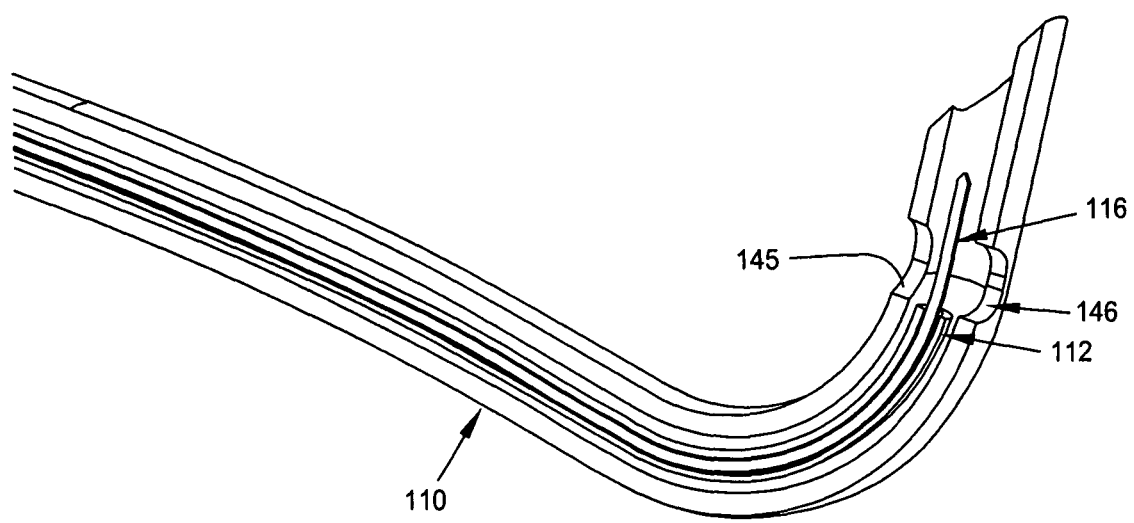
Figure 51:
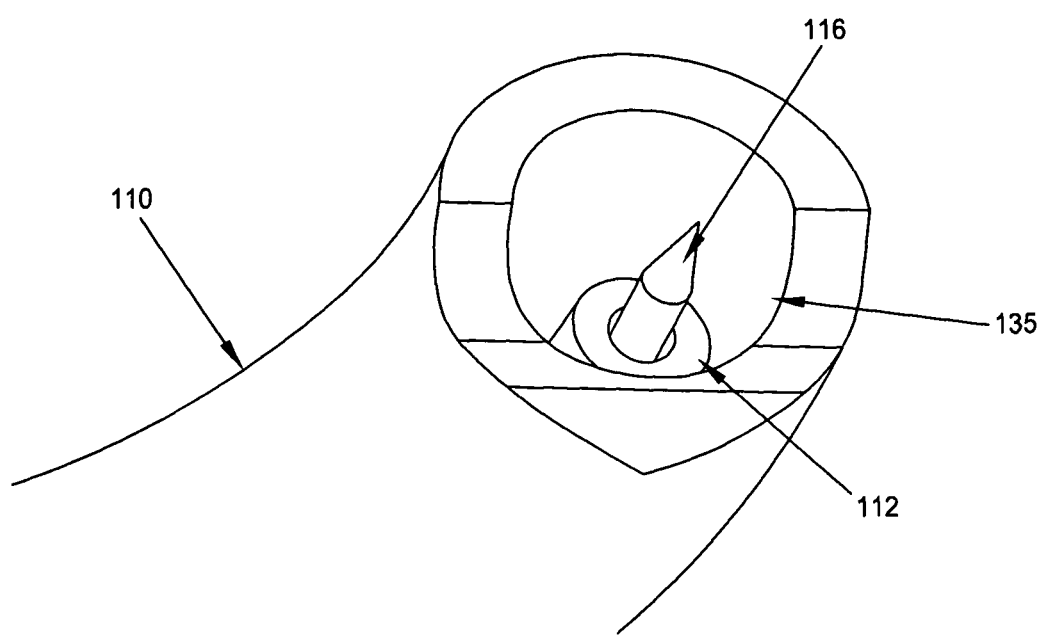

Outer shaft tube 110 further comprises a window 135 which extends radially into the outer shaft tube and communicates with lumen 130. Window 135 is sized so as to selectively receive a suture S therein, as will hereinafter be discussed in further detail. Window 135 comprises a pair of distal surfaces 140, a pair of proximal surfaces 145, and a pair of side surfaces 146. Preferably, distal surfaces 140 and proximal surfaces 145 extend substantially perpendicular to the longitudinal axis of outer shaft tube 110 (FIG. 49), and side surfaces 146 preferably extend substantially parallel to the longitudinal axis of outer shaft tube 110 (FIG. 50). Distal surfaces 140 are preferably spaced from proximal surfaces 145 by a distance which is somewhat larger than the diameter of suture S, so that window 135 provides an adequate seat for suture S, as will hereinafter be discussed in further detail.

Outer shaft tube 110 is preferably formed out of a substantially rigid material (e.g., stainless steel) so as to maintain rigidity when passing through tissue, particularly relatively tough fibrous tissue (e.g., the labrum of the hip).

In one preferred form of the present invention, the distal end 120 of outer shaft tube 110 is curved (see, for example, FIGS. 49, 58 and 59), however, it should also be appreciated that outer shaft tube 110 can be formed in other configurations well known in the art (e.g., straight, etc.).

Inner guide tube 112 comprises a distal end 150 and a proximal end 155, with a lumen 156 extending therebetween. Inner guide tube 112 is fixedly disposed within outer shaft tube 110 so that the distal end 150 of inner guide tube 112 terminates proximal to window 135 in outer shaft tube 110, with lumen 156 of inner guide tube 112 being substantially aligned with the center of window 135. The distal end 150 of inner guide tube 112 preferably terminates just proximal to window 135 of outer shaft tube 110. See, for example, FIGS. 50, 52 and 53. As will hereinafter be discussed, inner guide tube 112 acts as a guide and stiffening member for suture spear 116, which is selectively extendable out of the inner guide tube (and hence selectively extendable across window 135) and selectively withdrawable back into the inner guide tube (and hence selectively withdrawable out of window 135).

Figure 53:
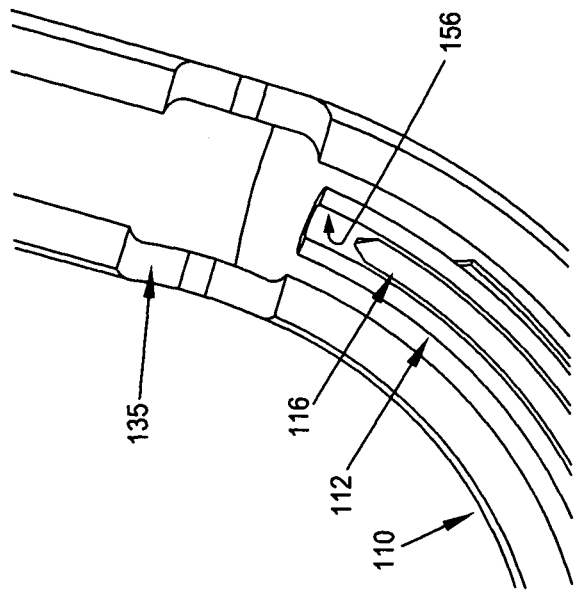
Figure 52:
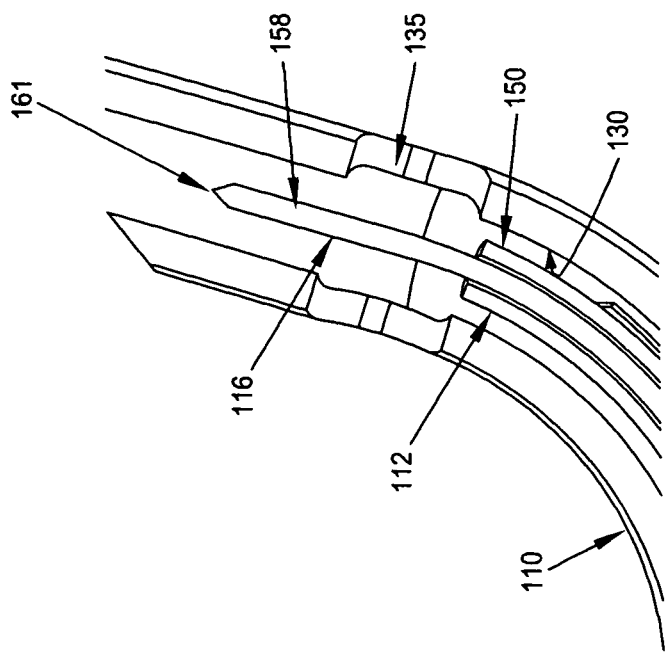
Figure 55:
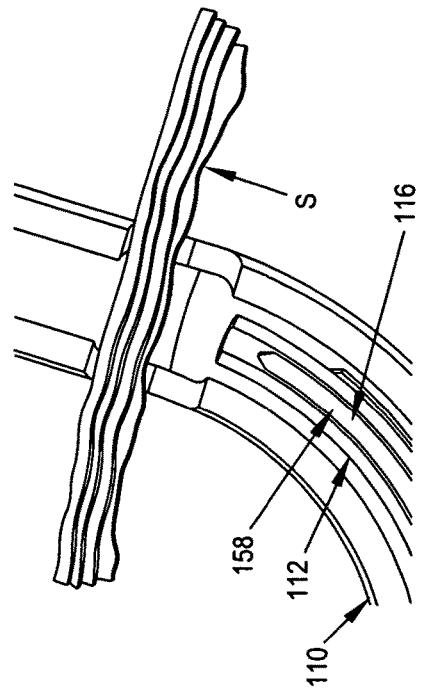

Suture spear 116 comprises a distal end 158 and a proximal end 159. Distal end 158 of suture spear 116 terminates in a point 161. It will be appreciated that suture spear 116 essentially comprises a needle which, as will hereinafter be discussed, is adapted to pierce suture. Suture spear 116 is slidably disposed within lumen 156 of inner guide tube 112, such that suture spear 116 can extend across window 135 (FIG. 52) or be withdrawn from window 135 (FIG. 53). Preferably the proximal end 159 of suture spear 116 extends out of the proximal end 155 of inner guide tube 112 and is connected to an actuator 172 (e.g., a thumb slide) which is movably mounted to handle 123, such that movement of actuator 172 relative to handle 123 will cause movement of suture spear 116 relative to inner guide tube 112 (and hence relative to outer shaft tube 110). Specifically, movement of actuator 172 relative to handle 123 will cause the distal end of suture spear 116 to intrude across, or be withdrawn from, window 135 of outer shaft tube 110.

It should be appreciated that the distal end of inner guide tube 112 is positioned within outer shaft tube 110 so that the inner guide tube (and hence the suture spear 116) is aligned with a suture S that is laid in window 135 so as to ensure that suture spear 116 can securely pierce the suture S, as will hereinafter be discussed.

Figure 54:
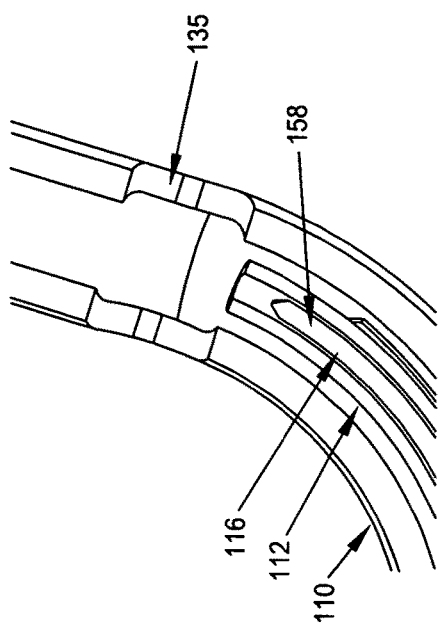
Figure 57:
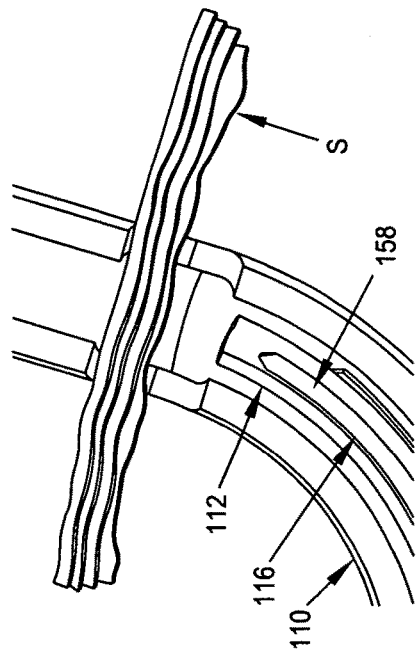
Figure 56:
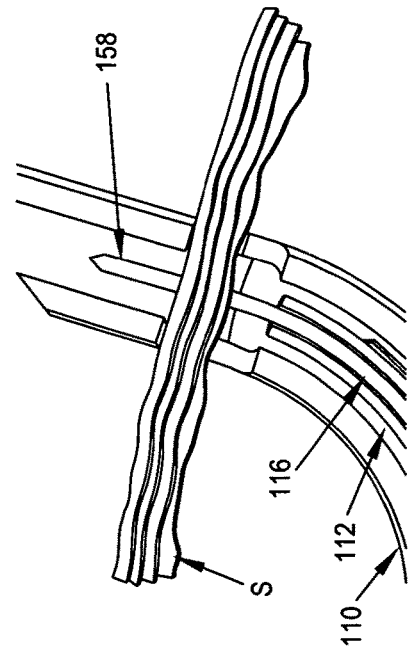
Figure 59:
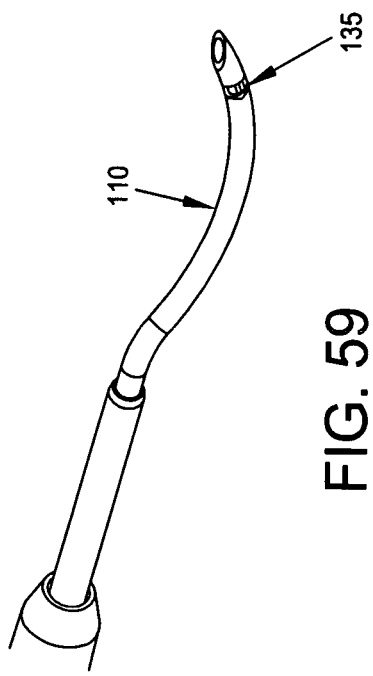
Figure 58:
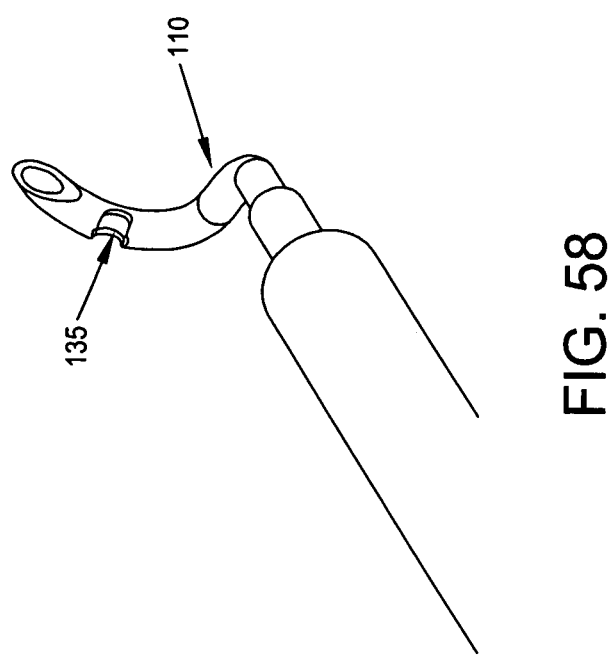
Figure 60:
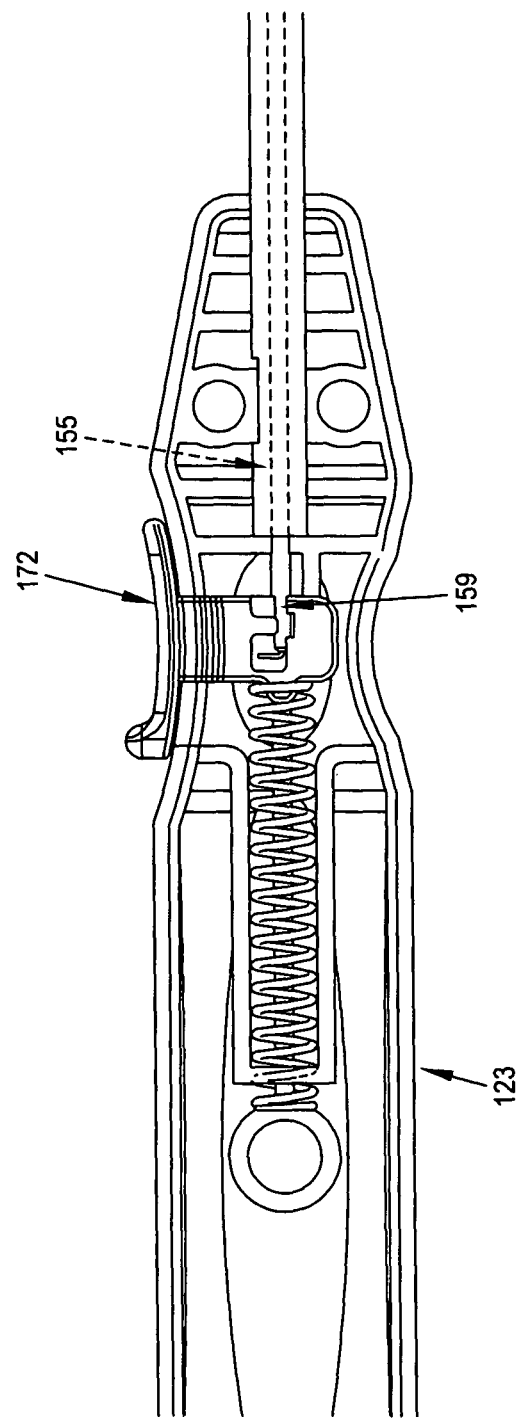

It will be appreciated that, on account of the foregoing construction, a piece of suture S may be clamped to the distal end of suture passer 105 by (i) moving suture spear 116 proximally so that the distal end 158 of suture spear 116 is withdrawn from window 135 of outer shaft tube 110, in the manner shown in FIG. 54 (e.g., by moving actuator 172 proximally relative to handle 123); (ii) positioning the suture S in window 135 (FIG. 55); and (iii) moving suture spear 116 distally (e.g., by moving actuator 172 distally relative to handle 123) so as to cause suture spear 116 to "spear" (e.g., penetrate) suture S, as shown in FIG. 56, whereby to secure suture S to suture passer 105.

It will also be appreciated that, on account of the foregoing construction, a speared piece of suture S (FIG. 56) may thereafter be released from suture passer 105 by (a) moving suture spear 116 proximally (FIG. 57) so as to "unspear" suture S; and (b) causing suture S to be withdrawn from window 135.

Using the Novel "Spear" Suture Passer to Pass Suture from the Near Side of Tissue to the Far Side of Tissue In one preferred form of the present invention, and looking now at FIGS. 61-64, the novel suture passer 105 can be used to pass suture S from the near side of tissue T to the far side of tissue T (i.e., in an "antegrade" manner).

More particularly, the preliminary loading of suture S into suture passer 105 may be performed away from the surgical site (e.g., outside of the patient) or it may be performed adjacent to the near side of the tissue T which is to be sutured (e.g., inside of the patient). As discussed previously, suture S may be loaded into suture passer 105 by retracting suture spear 116 out of window 135 of outer shaft tube 110 (FIG. 54), guiding suture S into window 135 (FIG. 55), and then advancing suture spear 116 distally through suture S (FIG. 56), whereby to secure suture S to suture passer 105. See FIG. 61.

Figure 62:
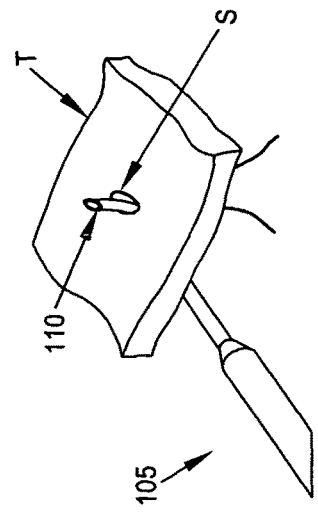
FIGS. 61-64 are schematic views showing an exemplary manner of passing suture using the novel suture passer of FIGS. 48-60.
Figure 64:
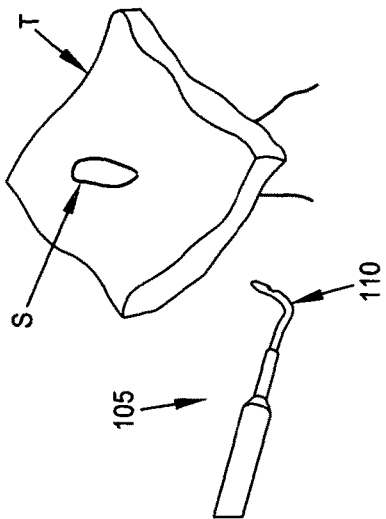
Figure 61:
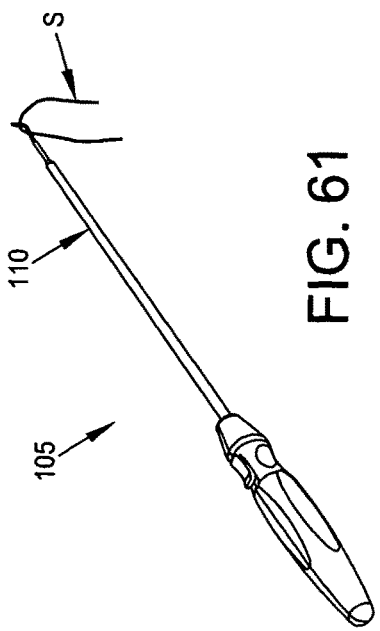
Figure 63:
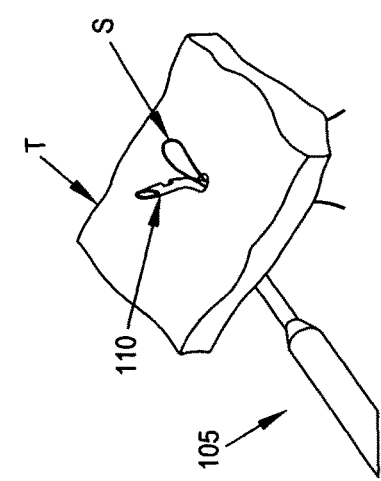

Suture passer 105 is then advanced distally so that window 135 passes through tissue T, whereby to carry suture S through the tissue (FIG. 62). With suture S extending through tissue T, and looking now at FIG. 63, suture spear 116 is retracted proximally so as to release suture S from suture passer 105, and then suture passer 105 and/or suture S are manipulated so that suture S is clear of window 135 (FIG. 63). Suture passer 105 may then be withdrawn back through tissue T, leaving suture S extending through tissue T, as shown in FIG. 64.

Using the Novel "Spear" Suture Passer to Draw Suture from the Far Side of Tissue to the Near Side of Tissue In another preferred form of the present invention, the spear suture passer 105 can be used to draw suture S from the far side of tissue T to the near side of tissue T (i.e., in a "retrograde" manner).

More particularly, in this form of the invention, the suture S is loaded into suture passer 5 on the far side of the tissue T. This is done by first passing suture passer 105 through tissue T so that window 135 resides on the far side of the tissue, and then moving suture spear 116 proximally so that suture spear 116 is withdrawn from window 135 (if the suture spear has not already been withdrawn from window 135). Suture S (disposed on the far side of tissue T) is then positioned into window 135, and suture spear 116 is advanced distally so as to spear suture S and secure the suture to suture passer 105. Outer shaft tube 110 is then retracted proximally through tissue T, carrying suture S therethrough. If desired, suture S can then be released from suture passer 105 by moving suture spear 116 distally.

Significantly, by alternating the aforementioned antegrade suture passing procedure (FIGS. 61-64) with the aforementioned retrograde suture passing procedure (discussed in the paragraph immediately preceding this paragraph), with the needle "plunges" being laterally spaced from one another in the tissue, a mattress stitch may be placed in the tissue, as will be appreciated by one skilled in the art.

If desired, the spear suture passer 105 may also be used to pass suture S around a side edge of the tissue T, rather than passing the suture S through the tissue. By way of example but not limitation, if the outer shaft tube 110 is passed around the side edge of the tissue (rather than through the tissue), the suture passer could then be used to retrieve the suture on the far side of the tissue and draw it back around the side edge of the tissue so that the suture is brought to the near side of the tissue.

As described above, the novel suture passer 105 has the ability to both pass (advance) and retrieve (draw) the suture S through and/or around the tissue in a continuous series of steps. This allows the surgeon to complete the desired suture passing without having to remove the suture passer 105 from the portal through which the suture passer 105 is being used. Significantly, this passing/retrieving process can be accomplished with a single instrument, rather than requiring one instrument for passing and a separate instrument for retrieving. This offers significant advantages in convenience and in reducing surgery time.

Figure 65:
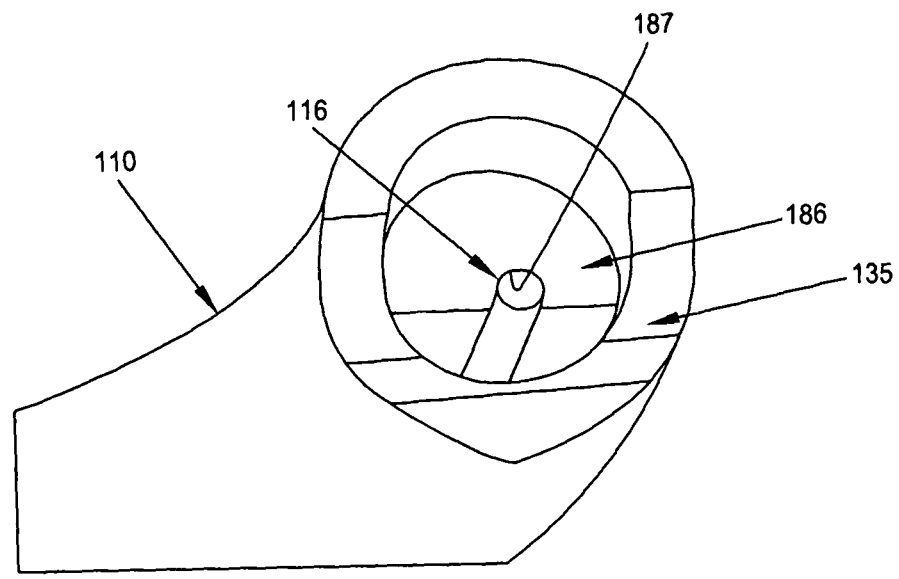
FIGS. 65-67 show variations of the novel suture passer shown in FIGS. 48-60.

If desired, the function of the inner guide tube 112 can be replaced by a rod 186 with a slot 187, as shown in FIG. 65. This rod 186 could also have other cross-sectional shapes (such as that of a ribbon, etc.) that act to constrain the suture spear 116 to the desired position relative to the window 135. This positioning scheme can also take the form of multiple wires filling the space where the suture spear is desired not to go.

Figure 66:
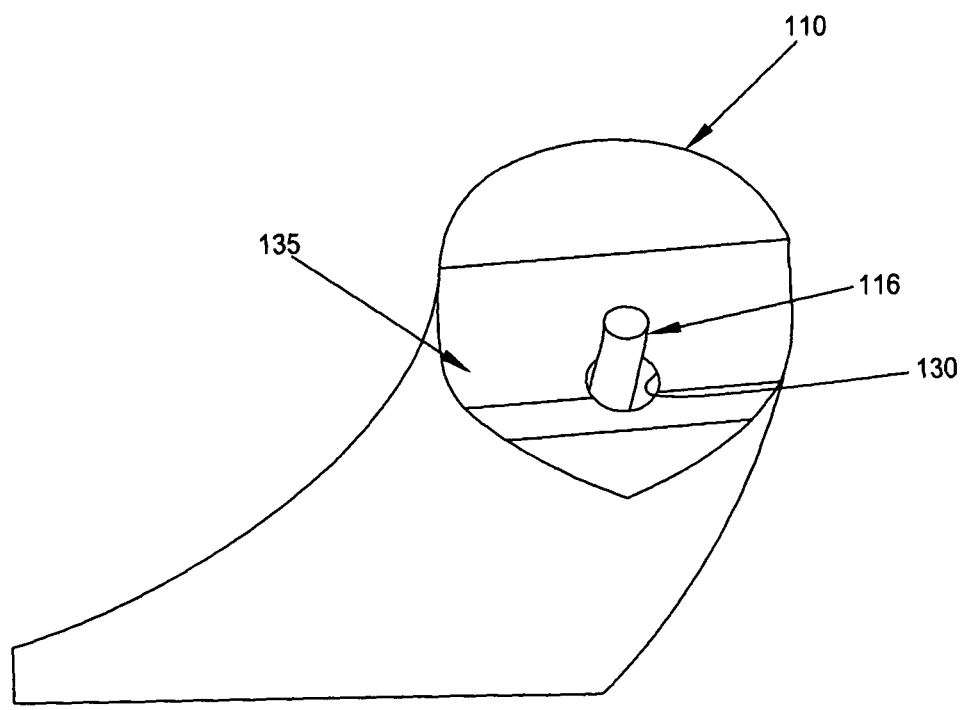

The function of inner guide tube 112 can also be incorporated into the outer shaft tube 110. For example, the outer shaft tube 110 can have a lumen 130 which is offset towards window 135, e.g., as shown in FIG. 66.

Figure 67:
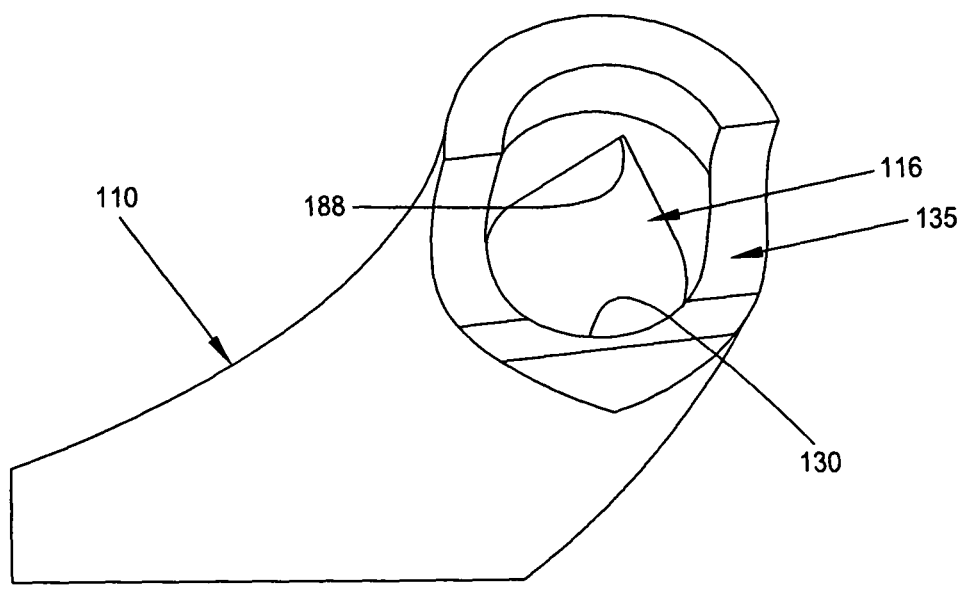

Additionally, suture spear 116 can occupy the entire internal diameter of lumen 130 of outer shaft tube 110. In this embodiment, and as shown in FIG. 67, the suture spear 116 is a rod with a sharpened feature 188 (e.g., a point) located in the window 135. In this embodiment, the inner guide tube 112 is not required.

Modifications

It should also be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A suture passer comprising:
a hollow tube, the hollow tube comprising a distal end, a proximal end, a lumen extending from the distal end to the proximal end, and a window formed in the sidewall of the hollow tube, the window being spaced from the distal end of the lumen, and the window having a distal surface and a proximal surface and communicating with the lumen; and
a clamping rod slidably received in the lumen of the hollow tube, the clamping rod comprising a distal end and a proximal end, the distal end consisting of a first arm including a hook and a second arm not including a hook, the first arm extending distally of the second arm, and the second arm being outwardly biased such that when the clamping rod is moved distally so that the distal end of the first arm is aligned with the lumen and the distal end of the outwardly biased second arm is adjacent to the window, the distal end of the outwardly biased second arm extends outwardly through the window so as to create a funnel region between the outwardly biased second arm and the hollow tube for guiding an object into the window, and when the clamping rod is moved proximally so that the hook of the first arm is adjacent to the window, the hook of the first arm clamps the object in the window against the proximal surface of the window.

2. A suture passer according to claim 1 wherein the distal end of the hollow tube comprises a point.

3. A suture passer according to claim 1 wherein the hollow tube is straight.

4. A suture passer according to claim 1 wherein the hollow tube is curved.

5. A suture passer according to claim 4 wherein the window is disposed on the inside of the curve of the hollow tube.

6. A suture passer according to claim 1 wherein at least one of the distal surface and the proximal surface is inclined.

7. A suture passer according to claim 6 wherein both the distal surface and the proximal surface are inclined.

8. A suture passer according to claim 1 wherein the distal surface and the proximal surface are inclined in the same direction.

9. A suture passer according to claim 8 wherein the distal surface and the proximal surface are inclined distally.

10. A suture passer according to claim 1 further comprising a handle connected to the proximal end of the hollow tube.

11. A suture passer according to claim 10 further comprising an actuator movably connected to the handle, the actuator being connected to the clamping rod.

12. A suture passer according to claim 1 wherein the hook faces proximally.

13. A suture passer according to claim 1 wherein the hook is inclined.

14. A suture passer according to claim 13 wherein the hook is inclined proximally.

15. A suture passer according to claim 1 wherein the hook is concave.

16. A suture passer according to claim 15 wherein the hook opens proximally.

17. A suture passer according to claim 1 wherein the distal end of the first arm is substantially blunt.

18. A suture passer according to claim 1 wherein the distal end of the first arm is pointed.

19. A suture passer according to claim 1 wherein the second arm is outwardly biased so as to extend at an angle of 10-120 degrees to the longitudinal axis of the hollow tube in the region of the window when the second arm extends out of the window.

20. A suture passer according to claim 19 wherein the second arm is outwardly biased so as to extend at an angle of 30-90 degrees to the longitudinal axis of the hollow tube in the region of the window when the second arm extends out of the window.

21. A suture passer according to claim 1 wherein the distal end of the first arm projects out of the hollow tube when the second arm projects out of the window.

22. A suture passer according to claim 1 wherein the distal surface of the window extends substantially perpendicular to the longitudinal axis of the hollow tube.

23. A suture passer comprising:
a hollow tube, the hollow tube comprising a distal end, a proximal end, a lumen extending from the distal end to the proximal end, and a window formed in the sidewall of the hollow tube, the window being spaced from the distal end of the lumen, and the window having a distal surface and a proximal surface and communicating with the lumen; and
a clamping rod slidably received in the lumen of the hollow tube, the clamping rod comprising a distal end and a proximal end, the distal end consisting of a first portion and a second portion, wherein the first portion includes a hook and the second portion does not include a hook, the second portion being outwardly biased such that when the clamping rod is moved distally so that the first portion of the distal end of the clamping rod is aligned with the lumen, and the second portion of the distal end of the clamping rod is adjacent to the window, the second portion of the distal end of the clamping rod extends outwardly through the window so as to create a funnel region between the outwardly biased distal end and the hollow tube for guiding an object into the window, and when the clamping rod is moved proximally so that the hook of the first portion of the distal end is adjacent to the window, the hook of the first portion of the distal end clamps the object in the window against the proximal surface of the window.

24. A suture passer according to claim 23 wherein the distal end of the hollow tube comprises a point.

25. A suture passer according to claim 23 wherein the hollow tube is straight.

26. A suture passer according to claim 23 wherein the hollow tube is curved.

27. A suture passer according to claim 26 wherein the window is disposed on the inside of the curve of the hollow tube.

28. A suture passer according to claim 23 wherein at least one of the distal surface and the proximal surface is inclined.

29. A suture passer according to claim 28 wherein both the distal surface and the proximal surface are inclined.

30. A suture passer according to claim 23 wherein the distal surface and the proximal surface are inclined in the same direction.

31. A suture passer according to claim 30 wherein the distal surface and the proximal surface are inclined distally.

32. A suture passer according to claim 23 further comprising a handle connected to the proximal end of the hollow tube.

33. A suture passer according to claim 32 further comprising an actuator movably connected to the handle, the actuator being connected to the clamping rod.

34. A suture passer according to claim 23 wherein the hook faces proximally.

35. A suture passer according to claim 34 wherein the hook is inclined proximally.

36. A suture passer according to claim 23 wherein the hook is inclined.

37. A suture passer according to claim 23 wherein the hook is concave.

38. A suture passer according to claim 37 wherein the hook opens proximally.

39. A suture passer according to claim 23 wherein the distal end of the first portion is substantially blunt.

40. A suture passer according to claim 23 wherein the distal end of the first portion is pointed.

41. A suture passer according to claim 23 wherein the second portion is outwardly biased so as to extend at an angle of 10-120 degrees to the longitudinal axis of the hollow tube in the region of the window when the second portion extends out of the window.

42. A suture passer according to claim 41 wherein the second portion is outwardly biased so as to extend at an angle of 30-90 degrees to the longitudinal axis of the hollow tube in the region of the window when the second portion extends out of the window.

43. A suture passer according to claim 23 wherein the distal end of the first portion projects out of the hollow tube when the second portion projects out of the window.

44. A suture passer according to claim 23 wherein the distal surface of the window extends substantially perpendicular to the longitudinal axis of the hollow tube.

* * * * *